United States Patent
Girdhar et al.

(10) Patent No.: US 12,318,126 B2
(45) Date of Patent: Jun. 3, 2025

(54) CURRENT GENERATOR FOR A MEDICAL TREATMENT SYSTEM

(71) Applicant: Covidien LP, Mansfield, MA (US)

(72) Inventors: Gaurav Girdhar, Costa Mesa, CA (US); Murali Krishna Marisetti, Hyderabad (IN); Manjit Singh Bindra, Hyderabad (IN); Hoai Nguyen, Westminster, CA (US)

(73) Assignee: COVIDIEN LP, Mansfield, MA (US)

( * ) Notice: Subject to any disclaimer, the term of this patent is extended or adjusted under 35 U.S.C. 154(b) by 991 days.

(21) Appl. No.: 17/304,829

(22) Filed: Jun. 25, 2021

(65) Prior Publication Data

US 2022/0409258 A1    Dec. 29, 2022

(51) Int. Cl.
*A61B 18/12* (2006.01)
*A61B 17/221* (2006.01)
*A61B 18/00* (2006.01)
*A61B 18/14* (2006.01)

(52) U.S. Cl.
CPC ........ *A61B 18/1206* (2013.01); *A61B 17/221* (2013.01); *A61B 2018/00077* (2013.01); *A61B 2018/00083* (2013.01); *A61B 2018/00178* (2013.01); *A61B 2018/00267* (2013.01); *A61B 2018/0041* (2013.01);
(Continued)

(58) Field of Classification Search
CPC ...... A61B 18/1206; A61B 2018/00178; A61B 2018/1823
See application file for complete search history.

(56) References Cited

U.S. PATENT DOCUMENTS

| 4,538,622 A | 9/1985 | Samson et al. |
| 5,167,239 A | 12/1992 | Cohen et al. |
| 5,549,626 A | 8/1996 | Miller et al. |

(Continued)

FOREIGN PATENT DOCUMENTS

| CN | 101472685 A | 7/2009 |
| CN | 102753106 A | 10/2012 |

(Continued)

OTHER PUBLICATIONS

Extended European Search Report dated Jul. 15, 2021; European Application No. 18888795.4; 6 pages.

(Continued)

*Primary Examiner* — Sean W Collins
(74) *Attorney, Agent, or Firm* — Fortem IP LLP

(57) ABSTRACT

A current generator for a medical treatment system is disclosed herein. In one example, the medical treatment system can include a cable and a current generator. The cable can include a distal portion that couples to a medical device and a proximal portion. The proximal portion of the cable can include a first and second conductor, with each conductor having an exposed contact region. The current generator can releasably couple to the cable to deliver an electrical signal. The current generator can include an inner chamber that can receive at least a portion of the cable. The current generator can also include first and second electrical connectors, which can electrically connect to the conductors. The current generator can also include a cable guide that can assist with position the cable within the inner chamber and a cable lock that can lock a part of the cable in position.

19 Claims, 13 Drawing Sheets

(52) U.S. Cl.
CPC ............... *A61B 2018/00422* (2013.01); *A61B 2018/1226* (2013.01); *A61B 2018/142* (2013.01)

(56) References Cited

U.S. PATENT DOCUMENTS

| | | |
|---|---|---|
| 5,662,671 A | 9/1997 | Barbut et al. |
| 5,885,278 A | 3/1999 | Fleischman |
| 5,891,136 A | 4/1999 | Mcgee et al. |
| 5,928,260 A | 7/1999 | Chin et al. |
| 5,972,019 A | 10/1999 | Engelson et al. |
| 6,022,336 A | 2/2000 | Zadno-Azizi et al. |
| 6,059,779 A | 5/2000 | Mills |
| 6,074,386 A * | 6/2000 | Goble ................ A61B 18/1402 606/42 |
| 6,102,908 A | 8/2000 | Tu et al. |
| 6,315,794 B1 | 11/2001 | Richter |
| 6,540,733 B2 | 4/2003 | Constantz et al. |
| 6,658,288 B1 | 12/2003 | Hayashi |
| 6,663,650 B2 | 12/2003 | Sepetka et al. |
| 6,837,886 B2 | 1/2005 | Collins et al. |
| 6,922,579 B2 | 7/2005 | Taimisto et al. |
| 7,094,249 B1 | 8/2006 | Broome et al. |
| 7,255,695 B2 | 8/2007 | Falwell et al. |
| 7,520,966 B2 | 4/2009 | Diaz et al. |
| 7,556,624 B2 | 7/2009 | Laufer et al. |
| 7,742,795 B2 | 6/2010 | Stone et al. |
| 8,032,222 B2 | 10/2011 | Loushin et al. |
| 8,038,674 B2 | 10/2011 | Schmaltz et al. |
| 8,246,641 B2 | 8/2012 | Osborne et al. |
| 8,249,685 B2 | 8/2012 | Falwell et al. |
| 8,382,821 B2 | 2/2013 | Richter |
| 8,603,014 B2 | 12/2013 | Alleman et al. |
| 8,795,305 B2 | 8/2014 | Martin et al. |
| 8,837,800 B1 | 9/2014 | Bammer et al. |
| 8,888,788 B2 | 11/2014 | Adams et al. |
| 8,965,534 B2 | 2/2015 | Hyatt et al. |
| 9,011,431 B2 | 4/2015 | Long et al. |
| 9,039,753 B2 | 5/2015 | Thramann |
| 9,119,656 B2 | 9/2015 | Bose et al. |
| 9,125,666 B2 | 9/2015 | Steinke et al. |
| 9,126,018 B1 | 9/2015 | Garrison |
| 9,179,971 B2 | 11/2015 | Kirschenman |
| 9,211,132 B2 | 12/2015 | Bowman |
| 9,241,699 B1 | 1/2016 | Kume et al. |
| 9,265,512 B2 | 2/2016 | Garrison et al. |
| 9,308,007 B2 | 4/2016 | Cully et al. |
| 9,399,118 B2 | 7/2016 | Kume et al. |
| 9,445,828 B2 | 9/2016 | Turjman et al. |
| 9,445,829 B2 | 9/2016 | Brady et al. |
| 9,492,637 B2 | 11/2016 | Garrison et al. |
| 9,539,022 B2 | 1/2017 | Bowman |
| 9,561,345 B2 | 2/2017 | Garrison et al. |
| 9,579,119 B2 | 2/2017 | Cully et al. |
| 9,585,741 B2 | 3/2017 | Ma |
| 9,642,635 B2 | 5/2017 | Vale et al. |
| 9,655,633 B2 | 5/2017 | Leynov et al. |
| 9,681,882 B2 | 6/2017 | Wilson et al. |
| 9,713,730 B2 | 7/2017 | Mathur et al. |
| 9,737,318 B2 | 8/2017 | Monstadt et al. |
| 9,770,251 B2 | 9/2017 | Bowman et al. |
| 9,795,400 B2 | 10/2017 | Davidson |
| 9,801,643 B2 | 10/2017 | Hansen et al. |
| 9,808,271 B2 | 11/2017 | Ulm |
| 9,827,084 B2 | 11/2017 | Bonnette et al. |
| 9,861,783 B2 | 1/2018 | Garrison et al. |
| 9,901,543 B2 | 2/2018 | Chausson et al. |
| 9,993,257 B2 | 6/2018 | Losordo et al. |
| 10,028,782 B2 | 7/2018 | Orion |
| 10,029,008 B2 | 7/2018 | Creighton |
| 10,039,906 B2 | 8/2018 | Kume et al. |
| 10,092,241 B2 | 10/2018 | Toth et al. |
| 10,136,942 B1 | 11/2018 | Cosman |
| 10,251,569 B2 | 4/2019 | Burkett |
| 10,413,309 B2 | 9/2019 | Farhat et al. |
| 10,660,698 B2 | 5/2020 | Willard et al. |
| 10,709,463 B2 | 7/2020 | Girdhar et al. |
| 10,847,411 B2 | 11/2020 | Chen et al. |
| 10,874,411 B2 | 12/2020 | Nguyen et al. |
| 10,987,117 B2 | 4/2021 | Girdhar et al. |
| 11,058,444 B2 | 7/2021 | Girdhar et al. |
| 11,090,071 B2 | 8/2021 | Girdhar et al. |
| 11,160,571 B2 | 11/2021 | Nguyen et al. |
| 11,523,838 B2 | 12/2022 | Nguyen et al. |
| 11,633,201 B2 | 4/2023 | Girdhar et al. |
| 11,666,350 B2 | 6/2023 | Nguyen et al. |
| 11,832,836 B2 | 12/2023 | Girdhar et al. |
| 11,944,332 B2 | 4/2024 | Girdhar et al. |
| 11,944,334 B2 | 4/2024 | Girdhar et al. |
| 11,944,374 B2 | 4/2024 | Girdhar et al. |
| 11,950,794 B2 | 4/2024 | Nguyen et al. |
| 11,963,713 B2 | 4/2024 | Girdhar et al. |
| 11,974,752 B2 | 5/2024 | Nguyen et al. |
| 12,004,803 B2 | 6/2024 | Nageswaran et al. |
| 12,016,582 B2 | 6/2024 | Nguyen et al. |
| 2001/0001314 A1 | 5/2001 | Davison et al. |
| 2001/0011182 A1 | 8/2001 | Dubrul et al. |
| 2002/0059938 A1 | 5/2002 | Fogarty et al. |
| 2002/0091407 A1 | 7/2002 | Zadno-azizi et al. |
| 2002/0133111 A1 | 9/2002 | Shadduck et al. |
| 2002/0138094 A1 | 9/2002 | Borillo et al. |
| 2003/0088245 A1 | 5/2003 | Woloszko et al. |
| 2003/0135232 A1 | 7/2003 | Douk et al. |
| 2004/0073243 A1 | 4/2004 | Sepetka et al. |
| 2004/0187875 A1 | 9/2004 | He et al. |
| 2004/0219660 A1 | 11/2004 | Dev et al. |
| 2005/0043728 A1 | 2/2005 | Ciarrocca |
| 2005/0090857 A1 | 4/2005 | Kusleika et al. |
| 2005/0096647 A1 | 5/2005 | Steinke et al. |
| 2005/0228417 A1 | 10/2005 | Teitelbaum et al. |
| 2006/0089638 A1 | 4/2006 | Carmel et al. |
| 2007/0005105 A1 | 1/2007 | Kusleika et al. |
| 2007/0208367 A1 | 9/2007 | Fiorella et al. |
| 2008/0042662 A1 | 2/2008 | Abraham |
| 2008/0045881 A1 | 2/2008 | Teitelbaum et al. |
| 2008/0262489 A1 | 10/2008 | Steinke et al. |
| 2008/0294181 A1 | 11/2008 | Wensel et al. |
| 2008/0300571 A1 | 12/2008 | Lepivert |
| 2009/0024154 A1 | 1/2009 | Williams et al. |
| 2009/0054918 A1 | 2/2009 | Henson |
| 2009/0069828 A1 | 3/2009 | Martin et al. |
| 2009/0112228 A1 | 4/2009 | Deshpande et al. |
| 2009/0171147 A1 * | 7/2009 | Lee ........................ A61B 17/29 600/137 |
| 2009/0198269 A1 | 8/2009 | Hannes et al. |
| 2009/0240250 A1 | 9/2009 | Hayashi et al. |
| 2009/0318892 A1 | 12/2009 | Aboytes et al. |
| 2009/0318943 A1 | 12/2009 | Eidenschink et al. |
| 2009/0318994 A1 | 12/2009 | Eidenschink et al. |
| 2010/0004623 A1 | 1/2010 | Hamilton et al. |
| 2010/0010533 A1 | 1/2010 | Burke et al. |
| 2010/0042136 A1 | 2/2010 | Berrada et al. |
| 2010/0168739 A1 | 7/2010 | Wu et al. |
| 2010/0174309 A1 | 7/2010 | Fulkerson et al. |
| 2010/0228280 A1 | 9/2010 | Groothuis et al. |
| 2010/0234842 A1 | 9/2010 | Schmaltz |
| 2010/0256616 A1 | 10/2010 | Katoh et al. |
| 2010/0256627 A1 | 10/2010 | Ma et al. |
| 2011/0130756 A1 | 6/2011 | Everson et al. |
| 2011/0196478 A1 | 8/2011 | Torosoff |
| 2011/0202085 A1 | 8/2011 | Loganathan et al. |
| 2011/0301506 A1 | 12/2011 | Volz |
| 2011/0301549 A1 | 12/2011 | Hartmann |
| 2011/0301594 A1 | 12/2011 | Orion et al. |
| 2012/0101560 A1 | 4/2012 | Kluck |
| 2013/0008780 A1 | 1/2013 | Andreacchi et al. |
| 2013/0030461 A1 | 1/2013 | Marks et al. |
| 2013/0072960 A1 | 3/2013 | Schneider et al. |
| 2013/0184702 A1 | 7/2013 | Neal et al. |
| 2013/0237864 A1 | 9/2013 | Mazar et al. |
| 2013/0281788 A1 | 10/2013 | Garrison |
| 2013/0282084 A1 | 10/2013 | Mathur et al. |
| 2013/0317589 A1 | 11/2013 | Martin et al. |
| 2013/0345739 A1 | 12/2013 | Brady et al. |

(56) References Cited

U.S. PATENT DOCUMENTS

| | | |
|---|---|---|
| 2014/0025069 A1 | 1/2014 | Willard et al. |
| 2014/0025152 A1 | 1/2014 | Headley |
| 2014/0172001 A1 | 6/2014 | Becking et al. |
| 2014/0180139 A1* | 6/2014 | Millett ................. A61B 5/6876 600/486 |
| 2014/0188127 A1 | 7/2014 | Dubrul et al. |
| 2014/0243882 A1 | 8/2014 | Ma |
| 2014/0257362 A1 | 9/2014 | Eidenschink |
| 2014/0265030 A1 | 9/2014 | Janardhan et al. |
| 2014/0276074 A1 | 9/2014 | Warner |
| 2014/0276778 A1 | 9/2014 | Mclawhorn et al. |
| 2014/0277013 A1 | 9/2014 | Sepetka et al. |
| 2014/0277079 A1 | 9/2014 | Vale et al. |
| 2014/0309673 A1 | 10/2014 | Dacuycuy et al. |
| 2014/0309675 A1 | 10/2014 | Maisano et al. |
| 2014/0343595 A1 | 11/2014 | Monstadt et al. |
| 2014/0364896 A1 | 12/2014 | Consigny |
| 2015/0112321 A1 | 4/2015 | Cadouri |
| 2015/0133990 A1 | 5/2015 | Davidson |
| 2015/0150672 A1 | 6/2015 | Ma |
| 2015/0164666 A1 | 6/2015 | Johnson et al. |
| 2015/0182740 A1 | 7/2015 | Mickelsen |
| 2015/0230820 A1 | 8/2015 | Turjman et al. |
| 2015/0297250 A1 | 10/2015 | Farhat et al. |
| 2015/0297251 A1 | 10/2015 | Sos |
| 2015/0359547 A1 | 12/2015 | Vale et al. |
| 2016/0008003 A1 | 1/2016 | Kleshinski et al. |
| 2016/0015402 A1 | 1/2016 | Brady et al. |
| 2016/0015935 A1 | 1/2016 | Chan et al. |
| 2016/0106448 A1 | 4/2016 | Brady et al. |
| 2016/0106449 A1 | 4/2016 | Brady et al. |
| 2016/0113663 A1 | 4/2016 | Brady et al. |
| 2016/0113665 A1 | 4/2016 | Brady et al. |
| 2016/0151618 A1 | 6/2016 | Powers et al. |
| 2016/0157843 A1 | 6/2016 | Dickson et al. |
| 2016/0157985 A1 | 6/2016 | Vo et al. |
| 2016/0199127 A1 | 7/2016 | Prutchi |
| 2016/0199620 A1 | 7/2016 | Pokorney et al. |
| 2016/0228681 A1 | 8/2016 | Di Palma et al. |
| 2016/0228684 A1 | 8/2016 | Martin |
| 2016/0242661 A1 | 8/2016 | Fischell et al. |
| 2016/0278839 A1 | 9/2016 | Pedersen et al. |
| 2016/0296690 A1 | 10/2016 | Kume et al. |
| 2016/0302808 A1 | 10/2016 | Loganathan et al. |
| 2016/0324440 A1 | 11/2016 | Kim et al. |
| 2016/0331377 A1 | 11/2016 | Divino et al. |
| 2016/0375180 A1 | 12/2016 | Anzai |
| 2017/0079766 A1 | 3/2017 | Wang et al. |
| 2017/0079767 A1 | 3/2017 | Leon-Yip |
| 2017/0086862 A1 | 3/2017 | Vale et al. |
| 2017/0100143 A1 | 4/2017 | Grandfield |
| 2017/0105743 A1 | 4/2017 | Vale et al. |
| 2017/0128126 A1 | 5/2017 | Sunenshine et al. |
| 2017/0164963 A1 | 6/2017 | Goyal |
| 2017/0172644 A1 | 6/2017 | Butzbacker et al. |
| 2017/0215902 A1 | 8/2017 | Leynov et al. |
| 2017/0215955 A1 | 8/2017 | Hancock et al. |
| 2017/0224953 A1 | 8/2017 | Tran et al. |
| 2017/0281909 A1 | 10/2017 | Northrop et al. |
| 2017/0290599 A1 | 10/2017 | Youn et al. |
| 2017/0311963 A1 | 11/2017 | Farhat et al. |
| 2017/0367707 A1 | 12/2017 | Divino |
| 2018/0049762 A1 | 2/2018 | Seip et al. |
| 2018/0084982 A1 | 3/2018 | Yamashita et al. |
| 2018/0116685 A1 | 5/2018 | Ulm, III |
| 2018/0116717 A1 | 5/2018 | Taff et al. |
| 2018/0132876 A1 | 5/2018 | Zaidat |
| 2018/0133436 A1 | 5/2018 | Garrison et al. |
| 2018/0140314 A1 | 5/2018 | Goyal et al. |
| 2018/0140315 A1 | 5/2018 | Bowman et al. |
| 2018/0140354 A1 | 5/2018 | Lam et al. |
| 2018/0161514 A1 | 6/2018 | Rothenberg et al. |
| 2018/0161541 A1 | 6/2018 | Haldis et al. |
| 2018/0185614 A1 | 7/2018 | Garrison et al. |
| 2018/0193026 A1 | 7/2018 | Yang et al. |
| 2018/0200040 A1 | 7/2018 | Wasdyke et al. |
| 2018/0236221 A1 | 8/2018 | Opie et al. |
| 2018/0303595 A1 | 10/2018 | Opie et al. |
| 2018/0344970 A1 | 12/2018 | Kornowski et al. |
| 2019/0038438 A1 | 2/2019 | John et al. |
| 2019/0046119 A1 | 2/2019 | Oxley |
| 2019/0175199 A1 | 6/2019 | Girdhar et al. |
| 2019/0175200 A1 | 6/2019 | Girdhar et al. |
| 2019/0239910 A1 | 8/2019 | Brady et al. |
| 2019/0262069 A1 | 8/2019 | Taff et al. |
| 2019/0336727 A1 | 11/2019 | Yang et al. |
| 2019/0388097 A1 | 12/2019 | Girdhar et al. |
| 2019/0388107 A1 | 12/2019 | Girdhar et al. |
| 2019/0388111 A1 | 12/2019 | Nguyen et al. |
| 2019/0388112 A1 | 12/2019 | Nguyen et al. |
| 2020/0054392 A1 | 2/2020 | Whiteley et al. |
| 2020/0129742 A1 | 4/2020 | Cope et al. |
| 2020/0297367 A1 | 9/2020 | Girdhar et al. |
| 2020/0297410 A1 | 9/2020 | Nguyen et al. |
| 2020/0390455 A1 | 12/2020 | Nguyen et al. |
| 2020/0390456 A1 | 12/2020 | Nguyen et al. |
| 2020/0390457 A1 | 12/2020 | Nageswaran et al. |
| 2020/0390458 A1 | 12/2020 | Nguyen et al. |
| 2021/0068853 A1 | 3/2021 | Nguyen et al. |
| 2021/0137542 A1 | 5/2021 | Oxley et al. |
| 2021/0177427 A1 | 6/2021 | Nguyen et al. |
| 2021/0177442 A1 | 6/2021 | Girdhar et al. |
| 2021/0177446 A1 | 6/2021 | Girdhar et al. |
| 2021/0186540 A1 | 6/2021 | Taff et al. |
| 2021/0238764 A1 | 8/2021 | Tyvoll et al. |
| 2021/0267612 A1 | 9/2021 | Girdhar et al. |
| 2021/0272676 A1 | 9/2021 | Dierl |
| 2022/0022899 A1 | 1/2022 | Girdhar et al. |
| 2022/0022900 A1 | 1/2022 | Nguyen et al. |
| 2022/0125455 A1 | 4/2022 | Girdhar et al. |
| 2022/0202431 A1 | 6/2022 | Davidson et al. |
| 2022/0218372 A1 | 7/2022 | Nguyen et al. |
| 2022/0236569 A1 | 7/2022 | Yamazaki et al. |
| 2022/0287616 A1 | 9/2022 | Dundovic et al. |
| 2022/0287765 A1 | 9/2022 | Nageswaran et al. |
| 2022/0313288 A1 | 10/2022 | Janardhan et al. |
| 2022/0387051 A1 | 12/2022 | Girdhar et al. |
| 2022/0387098 A1 | 12/2022 | Girdhar et al. |
| 2023/0064470 A1 | 3/2023 | Girdhar et al. |
| 2023/0113257 A1 | 4/2023 | Nguyen et al. |
| 2023/0149021 A1 | 5/2023 | Wainwright et al. |
| 2023/0277240 A1 | 9/2023 | Wu et al. |
| 2024/0074772 A1 | 3/2024 | Girdhar et al. |
| 2024/0081898 A1 | 3/2024 | Skillrud et al. |
| 2024/0293125 A1 | 9/2024 | Nguyen et al. |
| 2024/0315773 A1 | 9/2024 | Nageswaran et al. |

FOREIGN PATENT DOCUMENTS

| | | |
|---|---|---|
| CN | 104994799 A | 10/2015 |
| CN | 107405160 A | 11/2017 |
| CN | 104884681 B | 5/2018 |
| EP | 1484025 A1 | 12/2004 |
| EP | 2319575 B1 | 11/2013 |
| EP | 2490764 B1 | 9/2014 |
| EP | 2895645 A1 | 7/2015 |
| EP | 2967605 A1 | 1/2016 |
| EP | 3184067 A1 | 6/2017 |
| JP | 10290805 A | 11/1998 |
| JP | 2014004219 A | 1/2014 |
| JP | 2018118132 A | 8/2018 |
| KR | 20180102877 A | 9/2018 |
| WO | 9724073 A1 | 7/1997 |
| WO | 0035363 A1 | 6/2000 |
| WO | 2005000130 A1 | 1/2005 |
| WO | 2009127037 A1 | 10/2009 |
| WO | 2010061376 A1 | 6/2010 |
| WO | 2014079148 A1 | 5/2014 |
| WO | 2014168750 A1 | 10/2014 |
| WO | 2015141317 A1 | 9/2015 |
| WO | 2016007388 A1 | 1/2016 |
| WO | 2016141025 A1 | 9/2016 |
| WO | 2016198947 A1 | 12/2016 |
| WO | 2017058696 A1 | 4/2017 |

(56) References Cited

FOREIGN PATENT DOCUMENTS

| | | | |
|---|---|---|---|
| WO | 2017192999 | A1 | 11/2017 |
| WO | 2018019829 | A1 | 2/2018 |
| WO | 2018033401 | A1 | 2/2018 |
| WO | 2018046408 | A2 | 3/2018 |
| WO | 2018127796 | A1 | 7/2018 |
| WO | 2018137029 | A1 | 8/2018 |
| WO | 2018137030 | A1 | 8/2018 |
| WO | 2018145212 | A1 | 8/2018 |
| WO | 2018156813 | A1 | 8/2018 |
| WO | 2018172891 | A1 | 9/2018 |
| WO | 2018187776 | A1 | 10/2018 |
| WO | 2019102307 | A1 | 5/2019 |
| WO | 2019118321 | A1 | 6/2019 |
| WO | 2019133608 | A1 | 7/2019 |
| WO | 2019246377 | A2 | 12/2019 |
| WO | 2020174326 | A1 | 9/2020 |
| WO | 2021118868 | A1 | 6/2021 |
| WO | 2022058873 | A1 | 3/2022 |

OTHER PUBLICATIONS

International Search Report and Written Opinion mailed Feb. 26, 2021; International Application No. PCT/US20/63200; 14 pages.
International Search Report and Written Opinion mailed May 25, 2020, International Application No. PCT/US20/22463, 10 pages.
International Search Report and Written Opinion mailed Nov. 3, 2020, International Application No. PCT/US20/70142, 18 pages.
Fort, Stephen , et al., "'Fused-Gold' vs. 'Bare' stainless steel NIRflex stents of the same geometric design in diseased native coronary arteries. Long-term results from the NIR Top Study", Euro Interv 2007; 3:256-261.
International Search Report and Written Opinion dated Mar. 24, 2022; International Application No. PCT/US2021/061540; 10 pages.
https://www.merriam-webster.com/dictionary/affix (Year: 2022).
Chon, et al., "Mechanical behavior of rf-treated thrombus in mechanical thrombectomy", Qin Z, Kwok JC, Lam DC; Med Eng Phys. Sep. 2017;47:184-189. doi: 10.1016/j.medengphy.2017.06.011. Epub Jul. 5, 2017. PMID: 28688756. (Year: 2017).

* cited by examiner

CURRENT GENERATOR FOR A MEDICAL TREATMENT SYSTEM

TECHNICAL FIELD

The present technology relates to relates generally to devices, systems, and methods for removing obstructions from body lumens. Some embodiments of the present technology relate to devices and methods for a current generator for a medical treatment system.

BACKGROUND

Many medical procedures use medical device(s) to remove an obstruction (such as clot material) from a body lumen, vessel, or other organ. An inherent risk in such procedures is that mobilizing or otherwise disturbing the obstruction can potentially create further harm if the obstruction or a fragment thereof dislodges from the retrieval device. If all or a portion of the obstruction breaks free from the device and flows downstream, it is highly likely that the free material will become trapped in smaller and more tortuous anatomy. In many cases, the physician will no longer be able to use the same retrieval device to again remove the obstruction because the device may be too large and/or immobile to move the device to the site of the new obstruction.

Procedures for treating ischemic stroke by restoring flow within the cerebral vasculature are subject to the above concerns. The brain relies on its arteries and veins to supply oxygenated blood from the heart and lungs and to remove carbon dioxide and cellular waste from brain tissue. Blockages that interfere with this blood supply eventually cause the brain tissue to stop functioning. If the disruption in blood occurs for a sufficient amount of time, the continued lack of nutrients and oxygen causes irreversible cell death. Accordingly, it is desirable to provide immediate medical treatment of an ischemic stroke.

To access the cerebral vasculature, a physician typically advances a catheter from a remote part of the body (typically a leg) through the abdominal vasculature and into the cerebral region of the vasculature. Once within the cerebral vasculature, the physician deploys a device for retrieval of the obstruction causing the blockage. Concerns about dislodged obstructions or the migration of dislodged fragments increases the duration of the procedure at a time when restoration of blood flow is paramount. Furthermore, a physician might be unaware of one or more fragments that dislodge from the initial obstruction and cause blockage of smaller more distal vessels.

Many physicians currently perform thrombectomies (i.e. clot removal) with stents to resolve ischemic stroke. Typically, the physician deploys a stent into the clot in an attempt to push the clot to the side of the vessel and re-establish blood flow. Tissue plasminogen activator ("tPA") is often injected into the bloodstream through an intravenous line to break down a clot. However, it takes time for the tPA to reach the clot because the tPA must travel through the vasculature and only begins to break up the clot once it reaches the clot material. tPA is also often administered to supplement the effectiveness of the stent. Yet, if attempts at clot dissolution are ineffective or incomplete, the physician can attempt to remove the stent while it is expanded against or enmeshed within the clot. In doing so, the physician must effectively drag the clot through the vasculature, in a proximal direction, into a guide catheter located within vessels in the patient's neck (typically the carotid artery). While this procedure has been shown to be effective in the clinic and easy for the physician to perform, there remain some distinct disadvantages to using this approach.

For example, one disadvantage is that the stent may not sufficiently retain the clot as it pulls the clot to the catheter. In such a case, some or all of the clot might remain in the vasculature. Another risk is that, as the stent mobilizes the clot from the original blockage site, the clot might not adhere to the stent as the stent is withdrawn toward the catheter. This is a particular risk when passing through bifurcations and tortuous anatomy. Furthermore, blood flow can carry the clot (or fragments of the clot) into a branching vessel at a bifurcation. If the clot is successfully brought to the end of the guide catheter in the carotid artery, yet another risk is that the clot may be "stripped" or "sheared" from the stent as the stent enters the guide catheter.

In view of the above, there remains a need for improved devices and methods that can remove occlusions from body lumens and/or vessels.

SUMMARY

Mechanical thrombectomy (e.g., clot-grabbing and removal) has been effectively used for treatment of ischemic stroke. Although most clots can be retrieved in a single pass attempt, there are instances in which multiple attempts are needed to fully retrieve the clot and restore blood flow through the vessel. Additionally, there exist complications due to detachment of the clot from the interventional element during the retrieval process as the interventional element and clot traverse through tortuous intracranial vascular anatomy. For example, the detached clot or clot fragments can obstruct other arteries leading to secondary strokes. The failure modes that contribute to clot release during retrieval are: (a) boundary conditions at bifurcations; (b) changes in vessel diameter; and (c) vessel tortuosity, amongst others.

Certain blood components, such as platelets and coagulation proteins, display negative electrical charges. The treatment systems of the present technology provide an interventional element and a current generator configured to positively charge the interventional element during one or more stages of a thrombectomy procedure. For example, the current generator may apply a constant or pulsatile direct current (DC) to the interventional element. The positively charged interventional element attracts negatively charged blood components, thereby improving attachment of the thrombus to the interventional element and reducing the number of device passes or attempts necessary to fully retrieve the clot. In some aspects of the present technology, the treatment system includes an elongate core member (e.g., a cable) extending between the current generator and the interventional element. A delivery electrode may be integrated into the core member and/or interventional element, and the treatment system further includes a negative electrode that may be disposed at a number of different locations. For example, the negative electrode can be a wire coupled to or integrated within the core member. Additionally or alternatively, a negative electrode can take the form of a needle, a grounding pad, a conductive element carried by a one or more catheters of the treatment system, a separate guide wire, and/or any other suitable conductive element configured to complete an electrical circuit with the delivery electrode and the extracorporeally positioned current generator. When the interventional element is placed in the presence of blood (or any other electrolytic medium) and voltage is applied at the terminals of the current generator, current flows along the core member to the interventional element, through the blood, and to the return electrode, thereby positively charging at least a portion of the interventional element and adhering clot material thereto.

To avoid additional risk to the patient, and to ensure the treatment system functions properly, current should be reliably delivered to the interventional element. To improve reliability, a handheld current generator can be used to deliver current to the interventional element. In some embodiments, the handheld current generator can detachably couple to the core member to form an electrical connection. For example, the core member can be slidably inserted into the current generator so that some components of the core member come into contact with the electrical terminals of the current generator, which forms an electrical connection. In some embodiments, the current generator is sized so that an electrical connection is formed only when the core member is fully and properly inserted into the current generator. In various embodiments, the current generator can include several features that assist the user with reliably delivering current to the interventional element. For example, the current generator can include a guide surface that can guide the core element into the current generator and a locking mechanism that can hold the core element in position when a connection with the current generator is formed.

Additional features and advantages of the present technology are described below, and in part will be apparent from the description, or may be learned by practice of the present technology. The advantages of the present technology will be realized and attained by the structure particularly pointed out in the written description and claims hereof as well as the appended drawings. The subject technology is illustrated, for example, according to various aspects described below. Various examples of aspects of the subject technology are described as numbered clauses (1, 2, 3, etc.) for convenience. These are provided as examples and do not limit the subject technology 1. A medical system comprising:
   an elongate shaft comprising:
     a distal portion coupled to a medical device;
     a proximal portion;
     a first conductor including a first contact region at the proximal portion; and
     a second conductor having a second contact region at the proximal portion, the second contact region spaced apart from the first contact region; and
   a current source configured to be releasably coupled to the elongate shaft and deliver an electrical signal to the first and second conductors, the current source comprising:
     an inner chamber configured to receive at least the proximal portion of the elongate shaft;
     a first electrical connector disposed within the inner chamber and configured to electrically connect with the first conductor via the first contact region;
     a second electrical connector disposed within the inner chamber and configured to electrically connect with the second conductor via the second contact region;
     a cable guide positioned at one end of the current generator, the cable guide configured to guide the proximal portion of the cable to the inner chamber; and
     a cable lock configured to lock the at least a part of the elongate shaft in position.
2. The medical system of Clause 1, wherein the elongate shaft is sized and configured to be advanced through a corporeal lumen to a treatment site.
3. The medical system of Clause 1 or Clause 2, wherein the elongate shaft is sized and configured to be advanced intravascularly to a treatment site.
4. The medical system of any one of Clauses 1 to 3, wherein the elongate shaft has a diameter between 0.014 to 0.027 inches.
5. The medical system of any one of Clauses 1 to 4, wherein the first and second conductors are coaxial.
6. The medical system of any one of Clauses 1 to 5, wherein the elongate shaft is a cable.
7. The medical system of any one of Clauses 1 to 6, wherein the first conductor comprises a tubular member defining a lumen, and wherein the second conductor comprises an elongate member extending through the lumen.
8. The medical system of any one of Clauses 1 to 7, further comprising an electrically insulative material disposed radially between the first conductor and the second conductor.
9. The medical system of any one of Clauses 1 to 8, further comprising an electrically insulative material disposed axially between the first contact region and the second contact region.
10. The medical system of any one of Clauses 1 to 9, wherein the first conductor is insulated along at least a portion of its length and the second conductor is insulated along at least a portion of its length.
11. The medical system of Clause 10, wherein the first and second contact regions are uninsulated.
12. The medical system of any one of Clauses 1 to 11, wherein the first conductor is a hypotube.
13. The medical system of any one of Clauses 1 to 12, wherein the first electrical connector comprises an engagement surface.
14. The medical system of any one of Clauses 1 to 13, wherein the first electrical connector comprises a clip configured to contact the first contact region when the proximal portion of the cable is received within the inner chamber, and wherein the second electrical connector comprises a second clip configured to contact the second region when the proximal portion of the elongate shaft is received within the inner chamber.
15. The medical system of any one of Clauses 1 to 14, wherein the current source comprises a handheld device.
16. The medical system of any one of Clauses 1 to 15, wherein the current source comprises a battery.
17. The medical system of any one of Clauses 1 to 16, wherein the current source is configured to supply an electrical current of between about 0-5 mA for a time of between about 30 seconds to about 10 minutes.
18. The medical system of any one of Clauses 1 to 17, wherein the current source is a current generator.
19. The medical system of any one of Clauses 1 to 18, wherein the inner chamber comprises a proximal stop configured such that when the proximal portion of the elongate shaft is slidably disposed within the inner chamber such that a proximal end of the elongate shaft abuts the proximal stop, the first and second contact regions are in contact with the first and second connectors, respectively.
20. The medical system of any one of Clauses 1 to 19, wherein the cable guide comprises a guide surface adjacent an aperture, the guide surface configured to urge a proximal end of the elongate shaft through the aperture.

21. The medical system of Clause 20, wherein the guide surface is at least one of: tapered, curved, sloped, or conical.
22. The medical system of any one of Clauses 1 to 21, wherein the cable lock comprises an insert and a biasing mechanism, the biasing mechanism configured to urge the insert against the at least a part of the elongate shaft.
23. The medical system of Clause 22, wherein the insert is moveable between a locked and an unlocked position with respect to the cable.
24. The medical system of Clause 2222, wherein the insert is moveable along an axis that intersects a longitudinal axis of the cable.
25. The medical system of Clause 22, wherein the insert is biased in a locked configuration, the insert further comprising a release mechanism configured to temporarily move the insert away from contact with the at least a part of the cable.
26. The medical system of Clause 25, wherein the release mechanism comprises a depressible button.
27. The medical system of Clause 26, wherein the depressible button is integrally formed with the insert.
28. The medical system of Clause 25, wherein activating the release mechanism overcomes a bias of the biasing mechanism to release the at least a part of the cable.
29. The medical system of Clause 22, wherein the biasing mechanisms comprises one or more springs.
30. A current generator for a medical device including a core member, the current generator comprising:
a body having a first end, a second end opposite the first, and an inner chamber extending from the first end towards the second end, the inner chamber being configured to slidably connect to a core member and being configured to hold at least a part of the core member therein;
an electrical connector disposed at least partially within the inner chamber, the electrical connector configured to electrically connect with the core member;
a guide member positioned at the first end, the guide member configured to guide the at least a part of the core member to the inner chamber; and
a locking member configured to releasably retain the at least a part of the core member in position.
31. The current generator for a medical device of Clause 30, wherein the electrical connector comprises a clip configured to contact the core member.
32. The current generator for a medical device of Clause 30 or Clause 31, wherein the electrical connector comprises an engagement surface.
33. The current generator for a medical device of any one of Clauses 30 to 32, further comprising a second electrical connector disposed at least partially within the inner chamber.
34. The current generator for a medical device of any one of Clauses 30 to 33, wherein the guide member is tapered.
35. The current generator for a medical device of any one of Clauses 30 to 34, wherein the guide member is conical shaped.
36. The current generator for a medical device of any one of Clauses 30 to 35, wherein the locking member comprises an insert and a biasing mechanism, the biasing mechanism configured to press the insert against the at least a part of the core member.
37. The current generator for a medical device of Clause 36, wherein the insert is moveable between a locked and an unlocked position.
38. The current generator for a medical device of Clause 36, wherein the insert is moveable along an axis that intersects a longitudinal axis of the core member.
39. The current generator for a medical device of Clause 36, wherein the insert is biased in a locked configuration, the insert further comprising a release mechanism configured to temporarily move the insert away from contact with the at least a part of the cable.
40. The current generator for a medical device of Clause 39, wherein the release mechanism comprises a depressible button.
41. The current generator for a medical device of Clause 40, wherein the depressible button is integrally formed with the insert.
42. The current generator for a medical device of any one of Clauses 30 to 41, further comprising a battery electrically connected to the electrical connector.
43. The current generator for a medical device of any one of Clauses 30 to 42, wherein the current generator is configured to supply an electrical current of between about 0-5 mA for a time of between about 30 seconds to about 15 minutes.
44. The current generator for a medical device of any one of Clauses 30 to 43, wherein the inner chamber comprises a proximal stop configured to abut a proximal end of the core member such that when the core member abuts the proximal stop, the electrical connector electrically connects with the core member.
45. The current generator for a medical device of any one of Clauses 30 to 44, wherein the guide member comprises a guide surface adjacent an aperture, the guide surface configured to urge a proximal end of the core member through the aperture.
46. The current generator for a medical device of Clause 45, wherein the guide surface is at least one of: tapered, curved, sloped, or conical.
47. A method for delivering electrical current to a treatment device, the method comprising:
inserting a first end portion of a treatment device into a chamber of a current generator such that a first conductor of the treatment device is in electrical contact with a first electrical connector of the current generator and a second conductor of the treatment device is in electrical contact with a second electrical connector of the current generator;
locking the first end portion of the treatment device in position with respect to the current generator; and
delivering an electrical signal to the treatment device via the current generator.
48. The method of Clause 47, wherein inserting the first end portion of the treatment device into the chamber of the current generator comprises aligning an exposed portion of the first conductor with a first electrical connector of the current generator.
49. The method of Clause 48, wherein inserting the first end portion of the treatment device into the chamber of the current generator comprises aligning a second exposed portion of the second conductor with a second electrical connector of the current generator.
50. The method of any one of Clauses 47 to 49, wherein the electrical signal is delivered to the treatment device for two minutes or less.
51. The method of any one of Clauses 47 to 50, wherein the treatment device comprises a stent retriever.

52. The method of any one of Clauses 47 to 51, further comprising delivering the electrical signal to the treatment device via the current generator.

BRIEF DESCRIPTION OF THE DRAWINGS

Many aspects of the present disclosure can be better understood with reference to the following drawings. The components in the drawings are not necessarily to scale. Instead, emphasis is placed on clearly illustrating the principles of the present disclosure.

DETAILED DESCRIPTION

The present technology provides devices, systems, and methods for removing clot material from a blood vessel lumen. Although many of the embodiments are described below with respect to devices, systems, and methods for treating a cerebral or intracranial embolism, other applications and other embodiments, in addition to those described herein, are within the scope of the technology. For example, the treatment systems and methods of the present technology may be used to remove emboli from body lumens other than blood vessels (e.g., the digestive tract, etc.) and/or may be used to remove emboli from blood vessels outside of the brain (e.g., pulmonary, abdominal, cervical, or thoracic blood vessels, or peripheral blood vessels including those within the legs or arms, etc.). In addition, the treatment systems and methods of the present technology may be used to remove luminal obstructions other than clot material (e.g., plaque, resected tissue, foreign material, etc.). Moreover, the current generator of the present technology may be used in other contexts beyond removal of luminal obstructions, for example electrolytic detachment, neuromodulation, or any other instances in which electrical current is delivered to a treatment system disposed within a corporeal lumen or otherwise within the body.

Figure 1:
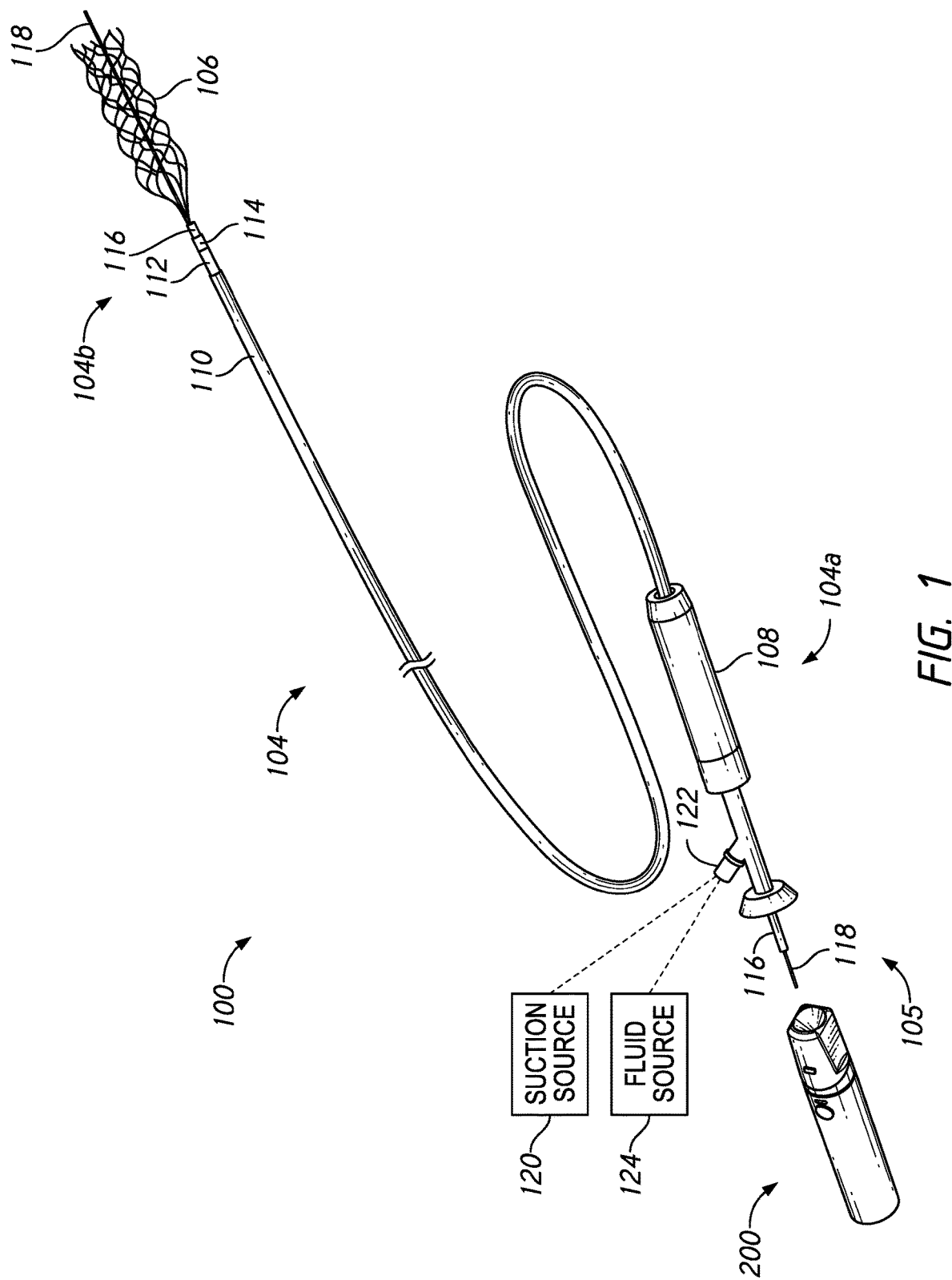
FIG. 1 shows a perspective view of an electrically enhanced treatment system for retrieving material from a body lumen, in accordance with the present technology.

FIG. 1 illustrates a view of an electrically enhanced treatment system 100 according to one or more embodiments of the present technology. As shown in FIG. 1, the treatment system 100 can include a current generator 200 and a treatment device 104 having a proximal portion 104a configured to be coupled to a core member 105 (see FIG. 2) and a distal portion 104b configured to be intravascularly positioned within a blood vessel (such as an intracranial blood vessel) at a treatment site at or proximate a thrombus. The treatment device 104 includes an interventional element 106 at the distal portion 104b, a handle 108 at the proximal portion 104a, a core member 105 coupled to the proximal portion 104a, and a plurality of elongated shafts or members extending therebetween. For example, in some embodiments, such as that shown in FIG. 1, the treatment device 104 includes a first catheter 110 (such as a guide catheter or balloon guide catheter), a second catheter 112 (such as a distal access catheter or aspiration catheter) configured to be slidably disposed within a lumen of the first catheter 110, and a third catheter 114 (such as a microcatheter) configured to be slidably disposed within a lumen of the second catheter 112.

The core member 105 is configured to be slidably disposed within the lumen of the third catheter 114. In the illustrated embodiment, the core member 105 can take the form of an electrical cable that includes a first conductor 116 and a second conductor 118. As discussed in more detail below, in some instances the first conductor 116 can take the form of an elongated tube (e.g., a hypotube) and the second conductor 118 can take the form of an elongated wire or rod. In some embodiments, the second conductor 118 is configured to be disposed within a lumen of the first conductor 116. The first conductor 116 and/or the second conductor 118 can be electrically insulated along at least a portion of their respective lengths. In some embodiments, the treatment device 104 does not include the second catheter 112. The first catheter 110 can be coupled to (or incorporate) the handle 108, which provides proximal access to the first conductor 116 and second conductor 118. In some embodiments, the handle 108 can be a series of rotating hemostasis valves. For example, the handle 108 can be a Bi-Tri-Quad axial system used for neurointerventions.

The current generator 200 may be coupled to the core member 105 to deliver electrical current to the interventional element 106 and thereby provide an electrically charged environment at the distal portion 104b of the treatment device 104. Further, the current generator 200 may be coupled to the core member 105 to return electrical current from the electrically charged environment to the current generator 200. In various embodiments, the current generator 200 can be electrically coupled to the first conductor 116, the second conductor 118, or both.

In some embodiments, the treatment system 100 includes a suction source 120 (e.g., a syringe, a pump, etc.) configured to be fluidically coupled (e.g., via a connector 122) to a proximal portion of one or more of the first catheter 110, the second catheter 112, and/or the third catheter 114 to apply negative pressure therethrough. In some embodiments, the treatment system 100 includes a fluid source 124 (e.g., a fluid reservoir, a syringe, pump, etc.) configured to be fluidically coupled (e.g., via the connector 122) to a proximal portion of one or more of the first catheter 110, the second catheter 112, and/or the third catheter 114 to supply fluid (e.g., saline, contrast agents, a drug such as a thrombolytic agent, etc.) to the treatment site.

According to some embodiments, the catheters 110, 112, and 114 can each be formed as a generally tubular member extending along and about a central axis. According to some embodiments, the third catheter 114 is generally constructed to track over a conventional guidewire in the cervical anatomy and into the cerebral vessels associated with the brain and may also be chosen according to several standard designs that are generally available. Accordingly, the third catheter 114 can have a length that is at least 125 cm long, and more particularly may be between about 125 cm and about 175 cm long. Other designs and dimensions are contemplated.

The second catheter 112 can be sized and configured to slidably receive the third catheter 114 therethrough. As noted above, the second catheter 112 can be coupled at a proximal portion to a suction source 120 (FIG. 1) such as a pump or syringe in order to supply negative pressure to a treatment site. The first catheter 110 can be sized and configured to slidably receive both the second catheter 112 and the third catheter 114 therethrough. In some embodiments, the first catheter 110 is a balloon guide catheter having an inflatable balloon or other expandable member surrounding the catheter shaft at or near its distal end. In operation the first catheter 110 can first be advanced through a vessel and then its balloon can be expanded to anchor the first catheter 110 in place and/or arrest blood flow from areas proximal of the balloon, e.g. to enhance the effectiveness of aspiration performed via the first catheter 110 and/or other catheter(s). (Alternatively, a guide catheter without a balloon can be employed.) Next, the second catheter 112 can be advanced through the first catheter 110 until its distal end extends distally beyond the distal end of the first catheter 110. The second catheter 112 can be positioned such that its distal end is adjacent a treatment site (e.g., a site of a blood clot within the vessel). The third catheter 114 may then be advanced through the second catheter 112 until its distal end extends distally beyond the distal end of the second catheter 112. The interventional element 106 may then be advanced through the third catheter 114 via the first conductor 116 for delivery to the treatment site.

According to some embodiments, the bodies of the catheters 110, 112, and 114 can be made from various thermoplastics, e.g., polytetrafluoroethylene (PTFE or TEFLON®), fluorinated ethylene propylene (FEP), high-density polyethylene (HDPE), polyether ether ketone (PEEK), etc., which can optionally be lined on the inner surface of the catheters or an adjacent surface with a hydrophilic material such as polyvinylpyrrolidone (PVP) or some other plastic coating. Additionally, either surface can be coated with various combinations of different materials, depending upon the desired results.

In some embodiments, the current generator 200 may be coupled to a proximal portion of the first conductor 116, and/or a proximal portion of the third catheter 114, the second catheter 112, and/or first catheter 110 to provide an electric current to the interventional element 106. For example, as shown in FIG. 1, the current generator 200 can be coupled to a proximal portion of the first conductor 116 such that the first conductor 116 functions as a first conductive path (e.g., as a positive conductive path transmitting current from the current generator to the treatment site). As shown in FIG. 1, the current generator 200 can also be coupled to a proximal portion of the second conductor 118 such that the second conductor 118 functions as a second conductive path (e.g., as a negative conductive path transmitting current from the treatment site to the current generator 102). In other embodiments, the negative electrode can be separate from the second conductor 118. In some embodiments, the positive electrode can comprise the interventional element 106, or a portion thereof, or be carried by the interventional element 106; the negative electrode can be carried by one or more of the third catheter 114, the second catheter 112, and/or first catheter 110, or be coupled to or formed by a portion of the second conductor 118. In some embodiments, the negative electrode can be provided via one or more external electrodes, such as a needle puncturing the patient, or a grounding pad applied to the patient's skin; in some such embodiments, the first conductor 116 or the second conductor 118 may be omitted from the core member 105.

The system can include multiple (e.g., two or more), distinct conductive paths or channels for passing electrical current along the system. The interventional element 106 can serve as one electrode (e.g., a positive electrode) in electrical communication with a conductive path via the first conductor 116. Another of the conductive paths of the system can be in electrical communication with another electrode (e.g., a negative electrode). For example, the second conductor 118 can serve as the negative electrode.

Figure 2:
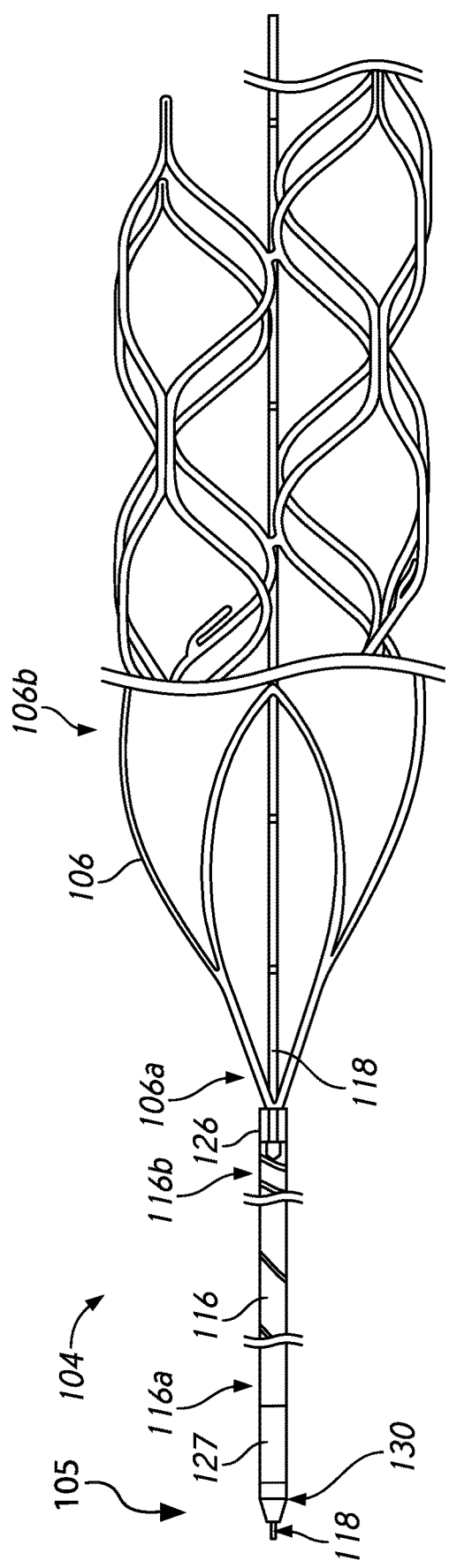
FIG. 2 shows a side schematic view of the treatment device for retrieving material from a body lumen, in accordance with one or more embodiments of the present technology.

As shown in FIG. 2, the first conductor 116 and the interventional element 106 can be joined at a connection 126 to secure the interventional element 106 relative to the first conductor 116 and to complete an electrical pathway between the elongate first conductor 116 to the interventional element 106. The interventional element 106 can be metallic or otherwise electrically conductive so that when the interventional element 106 is placed in the presence of blood (or thrombus, and/or any other electrolytic medium which may be present, such as saline) and voltage is applied via the electrical connectors of the current generator 200, current flows from the positive connector of the current generator 200, distally along the first conductor 116 to the interventional element 106 and through the surrounding media (e.g., blood, tissue, thrombus, etc.) before returning proximally along the second conductor 118 to the negative electrical connector of the current generator 200, thereby positively charging at least a portion of the interventional element 106 and promoting clot adhesion.

In various embodiments, the second conductor 118 and the interventional element 106 can be joined together to secure the interventional element 106 relative to the second conductor 118 and to complete an electrical pathway between the elongate second conductor 118 to the interventional element 106. For example, when voltage is applied via the electrical connectors of the current generator 200, current can flow from the positive connector of the current generator 200, distally along the second conductor 118 to the interventional element 106 and through the surrounding media (e.g., blood, tissue, thrombus, etc.) before returning proximally along the first conductor 116 to the negative electrical connector of the current generator 200, thereby positively charging at least a portion of the interventional element 106 and promoting clot adhesion.

In certain embodiments, the polarities of the current generator 200 can be switched, so that the negative electrical connector is electrically coupled to the first conductor 116 and the positive electrical connector is electrically coupled to the second conductor 118. This can be advantageous when, for example, attempting to attract predominantly positively charged material to the interventional element 106, or when attempting to break up a clot rather than grasp it with an interventional element 106. In some embodiments alternating current (AC) signals may be used rather than DC. In certain instances, AC signals may advantageously help break apart a thrombus or other material.

In various embodiments, the interventional element 106 can take any number of forms, for example a removal device, a thrombectomy device, or other suitable medical device. For example, in some embodiments the interventional element 106 may be a stent and/or stent retriever, such as Medtronic's Solitaire™ Revascularization Device, Stryker Neurovascular's Trevo® ProVue™ Stentriever, or other suitable devices. In some embodiments, the interventional element 106 may be a coiled wire, a weave, and/or a braid formed of a plurality of braided filaments. Examples of suitable interventional elements 106 include any of those disclosed in U.S. Pat. No. 7,300,458, filed Nov. 5, 2007, U.S. Pat. No. 8,940,003, filed Nov. 22, 2010, U.S. Pat. No. 9,039,749, filed Oct. 1, 2010, and U.S. Pat. No. 8,066,757, filed Dec. 28, 2010, each of which is incorporated by reference herein in its entirety.

The interventional element 106 can have a low-profile, constrained or compressed configuration for intravascular delivery to the treatment site within the third catheter 114, and an expanded configuration for securing and/or engaging clot material and/or for restoring blood flow at the treatment site. The interventional element 106 has a proximal portion including an attachment portion 106a that may be coupled to the first conductor 116 and a distal portion comprising an open cell framework or body 106b. In some embodiments, the body 106b of the interventional element 106 can be generally tubular (e.g., cylindrical), and the proximal portion of the interventional element 106 can taper proximally to the attachment portion 106a.

The interventional element 106 can be a metallic and/or electrically conductive thrombectomy device. For example, the interventional element can include or be made of stainless steel, nitinol, cobalt-chromium, platinum, tantalum, alloys thereof, or any other suitable material. In some embodiments, the interventional element 106 is a mesh structure (e.g., a braid, a stent, etc.) formed of a superelastic material (e.g., Nitinol) or other resilient or self-expanding material configured to self-expand when released from the third catheter 114. The mesh structure may include a plurality of struts and open spaces between the struts. In some embodiments, the struts and spaces may be situated along the longitudinal direction of the interventional element 106, the radial direction, or both.

In some embodiments, the first conductor 116 can be a structural element configured to push and pull a device such as the interventional element 106 along the bodily lumen. The first conductor 116 can be any suitable elongate member configured to advance the interventional element 106 to a treatment site within a blood vessel. For example, the first conductor 116 can be or include a wire, tube (e.g., a hypotube), coil, or any combination thereof. According to some embodiments, the first conductor 116 comprises an elongate tubular member defining a lumen therethrough. In some embodiments, the first conductor 116 can comprise a distally located aperture configured to receive the attachment portion of the interventional element. In some embodiments, the first conductor 116 comprises a distally located joining element comprising the aperture configured to receive the attachment portion. The first conductor 116 can have a length sufficient to extend from a location outside the patient's body through the vasculature to a treatment site within the patient's body. The first conductor 116 can be a monolithic structure or formed of multiple joined segments. In some embodiments, the first conductor 116 can comprise a laser-cut hypotube having a spiral cut pattern (or other pattern of cut voids) formed in its sidewall along at least a portion of its length. The first conductor 116 can be metallic and/or otherwise electrically conductive to deliver current from the current generator 102 to the interventional element 106. For example, the first conductor 116 can comprise or consist of nickel titanium alloy, stainless steel, or other metals or alloys. In embodiments that comprise multiple joined segments, the segments may be of the same or different materials. For example, some or all of the first conductor 116 can be formed of stainless steel, or other suitable materials known to those skilled in the art. Nickel titanium alloy may be preferable for kink resistance and reduction of imaging artifacts.

In some embodiments, the second conductor 118 can be a structural element configured to secure or retain a position of the interventional element 106 relative to the first conductor 116. Additionally, or alternatively, the second conductor 118 can be configured to be a negative electrode. The second conductor 118 can be any suitable elongate member configured to extend through a lumen of the first conductor 116. For example, the second conductor 118 can be or include a wire, tube (e.g., a hypotube), coil, or any combination thereof. The second conductor 118 can have a length sufficient to extend from a location outside the patient's body through the vasculature to a treatment site within the patient's body. The second conductor 118 can be a monolithic structure or formed of multiple joined segments. The second conductor 118 can be metallic or electrically conductive to deliver current from the surrounding media (e.g., blood, tissue, thrombus, etc.) to the current generator 200. For example, the second conductor 118 can comprise or consist of nickel titanium alloy, stainless steel, or other metals or alloys. In embodiments that comprise multiple joined segments, the segments may be of the same or different materials. For example, some or all of the second conductor 118 can be formed of stainless steel, or other suitable materials known to those skilled in the art. Nickel titanium alloy may be preferable for kink resistance and reduction of imaging artifacts. The second conductor 118 can be electrically insulated along some or all of its length. In some embodiments, the second conductor 118 comprises an insulated wire or guide wire having one or more exposed, electrically conductive portions. For example, a distal end portion of the second conductor 118 can be exposed to conduct current from surrounding media (e.g., blood, tissue, thrombus, etc.) at a treatment site.

In some embodiments, the treatment device 104 can comprise one or more electrically insulating materials. For example, an insulating material 130 can be disposed on one or more portions of the second conductor 118 to electrically isolate the second conductor 118 from the first conductor 116, the connection 126, and/or the interventional element 106. Additionally or alternatively, the insulating material 130 can be disposed within a lumen of the first conductor 116 to electrically isolate the first conductor 116 from the second conductor 118 and/or the attachment portion of the interventional element 106. In some embodiments, the insulating material 130 is disposed over an outer surface of the first conductor 116 along at least a portion of a length of the first conductor 116 to direct current through the first conductor 116 and prevent current loss from the first conductor 116 to the surrounding environment. As shown in FIG. 2, in some embodiments, an insulating material 127 can be disposed adjacent to a proximal end portion 116a and/or a distal end portion 116b of the first conductor 116. The insulating material 127 may be disposed along an entire length of the first conductor 116 and/or the second conductor 118 or the insulating material may be disposed along select portions of the first conductor 116 and/or the second conductor 118. The insulating materials 127, 130 may comprise polyimide, parylene, PTFE, or another suitable electrically insulating material.

As shown in FIG. 2, the interventional element 106 and the first conductor 116 can be coupled at a connection 126. According to some embodiments, the interventional element 106 and the first conductor 116 can be substantially permanently attached together at the connection 126. That is, the interventional element 106 and the first conductor 116 can be attached together in a manner that, under the expected use conditions of the device, the interventional element 106 and the first conductor 116 would not become unintentionally separated from one another. In some embodiments, the treatment device 104 can comprise a portion, located proximally or distally of the connection 126, that is configured for selective detachment of the interventional element 106 from the first conductor 116. For example, such a portion can comprise an electrolytically severable segment of the first conductor 116. In some embodiments, the device can be devoid of any feature that would permit selective detachment of the interventional element 106 from the first conductor 116. The connection 126 can provide a mechanical interlock between the interventional element 106 and the first conductor 116. Moreover, the connection 126 can be configured to complete an electrically conductive path between the interventional element 106 and the elongate first conductor 116.

In some embodiments, the connection 126 can comprise a bonding agent and/or a joining element. The bonding agent can comprise adhesive, solder, welding flux, brazing filler, etc. In some embodiments, the bonding agent can bond to the connection 126 without applying heat. For example, the bonding agent can comprise a UV-curable adhesive. In embodiments that comprise a polymer coating of the wire or polymer tubing, use of a bonding agent that avoids application of heat that would damage the polymer may be preferred. The joining element can be mechanical component used to mechanically interlock the interventional element 106 to the connection 126.

Figure 3A:
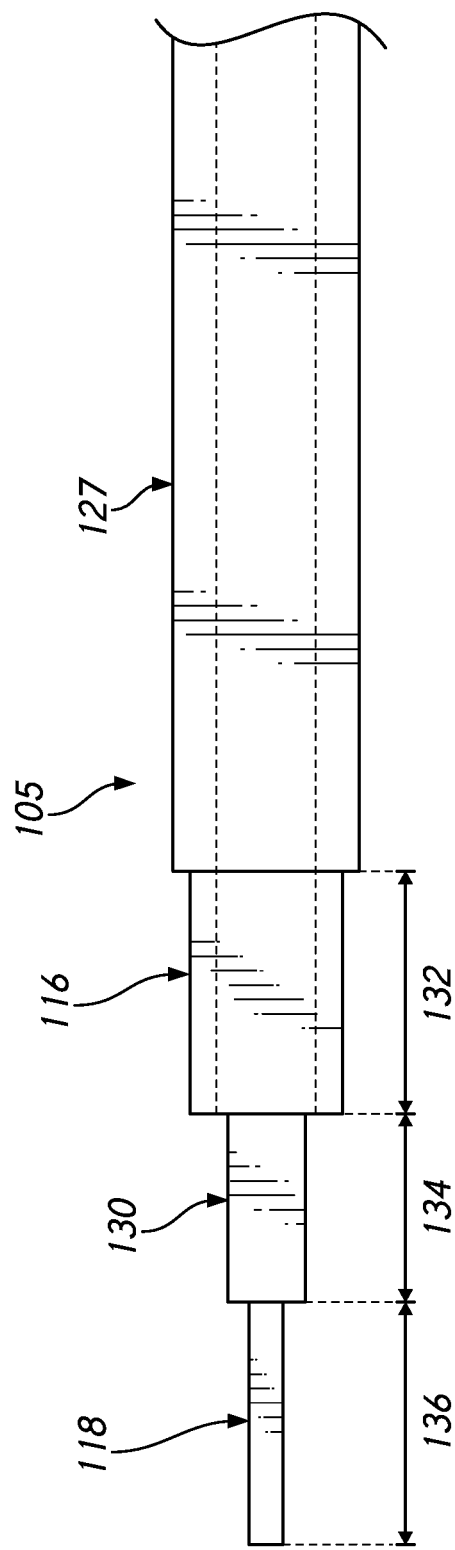
FIG. 3A shows a side schematic view of a core member, in accordance with one or more embodiments of the present technology.

FIG. 3A illustrates a schematic view of a proximal end of the core member 105 according to one or more embodiments of the present technology. The illustrated proximal portion of the core member 105 can include an insulating material 127, the proximal end of the first conductor 116, an insulating material 130, and the proximal end of the second conductor 118. The insulating material 127 can be disposed radially around the distal portion of the first conductor 116. The first conductor 116 can form a lumen, with the insulating material 130 and second conductor 118 disposed within the lumen of the first conductor. The insulating material 130 can be disposed radially between the first conductor 116 and the second conductor 118. In some embodiments, the core member 105 can be arranged in a cable-like manner. For example, insulating material 127 can function as a cable sheath, with the first conductor 116, insulating material 130, and second conductor 118 disposed within the insulating material 127. In some embodiments, the insulating material 127, the first conductor 116, an insulating material 130, and the second conductor 118 can be arranged coaxially. In some embodiments, the insulating material 127, the first conductor 116, an insulating material 130, and the second conductor 118 can be parallel to one or more of the components of the core member 105.

In some embodiments, sections (e.g., proximal end sections) of the first conductor 116 and the second conductor 118 can be uninsulated, and thus, exposed. For example, as shown in FIG. 3A, the first conductor 116 can be uninsulated along the length 132. Additionally, or alternatively, the second conductor 118 can be uninsulated along the length 136. The exposed portions of the first conductor 116 and second conductor 118 can form a contact region that can allow for a separate component, such as an electrical clip or other electrical connector, to contact the exposed portions. In some embodiments, the first conductor 116 and second conductor 118 can be configured to be exposed at different locations along a longitudinal axis of the core member 105. For example, in some embodiments, a portion of the insulating material 130 can be axially positioned in between the first conductor 116 and the second conductor 118 such that the insulating material 130 separates the exposed portions of the first conductor 116 and the second conductor 118 along the length 134. In some embodiments, the first conductor 116 can have an exposed contact region at or near the proximal end or portion of the core member 105. In various embodiments, the second conductor 118 can have an exposed contact region at or near the proximal end or portion of core member 105.

In some embodiments, the core member 105 can be configured to receive an electrical signal from the current generator 200. For example, as will be described in more detail below, one or more electrical connectors from the current generator 200 can electrically connect with the contact regions of first conductor 116 and second conductor 118 to deliver an electrical signal to the first conductor 116 and the second conductor 118.

Figure 3B:
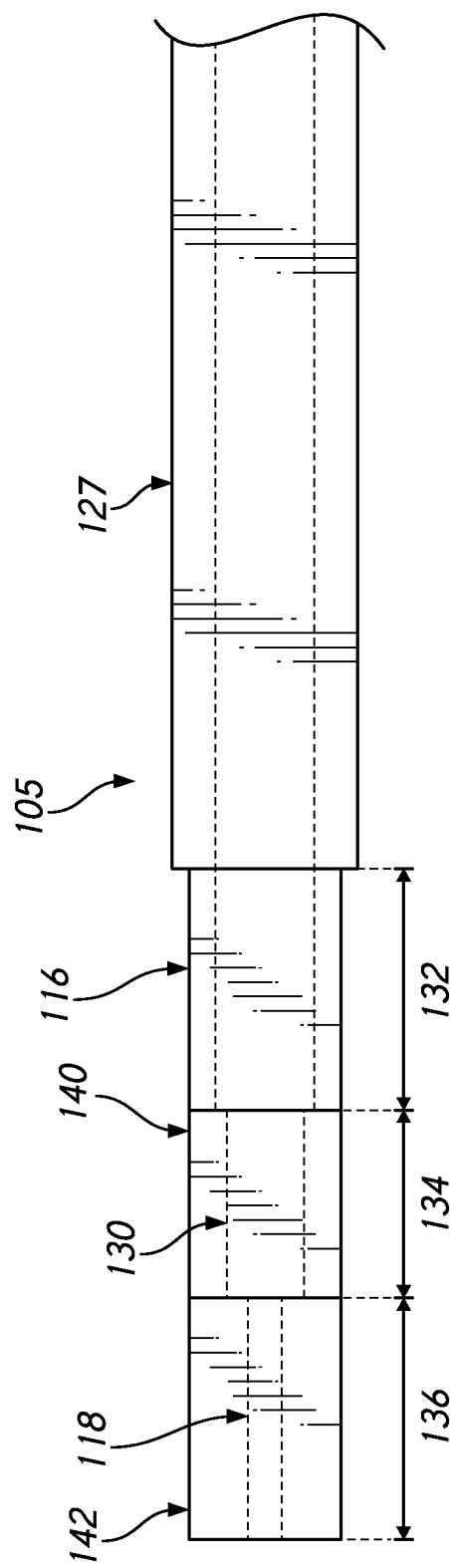
FIG. 3B shows a side schematic view of a core member, in accordance with one or more embodiments of the present technology.

In some embodiments, an insulative or conductive tube can be coupled to the first conductor 116, second conductor 118, and insulating material 130. As illustrated in FIG. 3B, proximal portion of the core member 105 can include an insulating material 127, the proximal end of the first conductor 116, an insulating tube 140, and a conductive tube 142. The insulating tube 140 can be coupled to the insulating material 130 so that the insulating tube 140 is disposed radially around the proximal end of the insulating material 130. The conductive tube 142 can be coupled to the proximal end of the second conductor 118 so that the conductive tube 142 is disposed radially around the proximal end of the second conductor 118. In some embodiments, the insulative tube 140 and the conductive tube 142 can be coupled to the core member 105 in a manner that creates a substantially uniform width at the proximal end of the core member 105. For example, as illustrated in FIG. 3B, the first conductor 116, insulative tube 140, and conductive tube 142 can have substantially the same outer diameter, which creates substantially a uniform width at the proximal end of the core member 105. In various embodiments, the proximal end of the core member 105 can have a non-uniform width. For example, the insulative tube 140 can have a larger outer diameter than the conductive tube 142 or the first conductor 116.

In some embodiments, insulative tube 140 can prevent electrical shortages between the first conductor 116, the second conductor 118, and/or the conductive tube 142 at the proximal end of the core member 105. For example, the conductive tube 140 can include an electrically insulative material and can be positioned between the first conductor 116 and the second conductor 118 and/or conductive tube 142. This arrangement can prevent the first conductor 116 from directly contacting the second conductor 118 or the conductive tube 142.

In some embodiments, the conductive tube 142 can assist with coupling the current generator 200 to the second conductor 118. For example, the conductive tube 142 can include an electrically conductive material that allows for the conductive tube 142 and the second conductor 118 to be electrically coupled. Additionally, in some embodiments, the outer surface of the conductive tube 142 can be electrically conductive, which can allow for an electrical signal to be delivered to the second conductor 118 through the conductive tube 142. This arrangement can allow for one or more electrical connectors from the current generator 200 to electrically couple with the second conductor 118 by coupling with the conductive tube 142.

Figure 4:
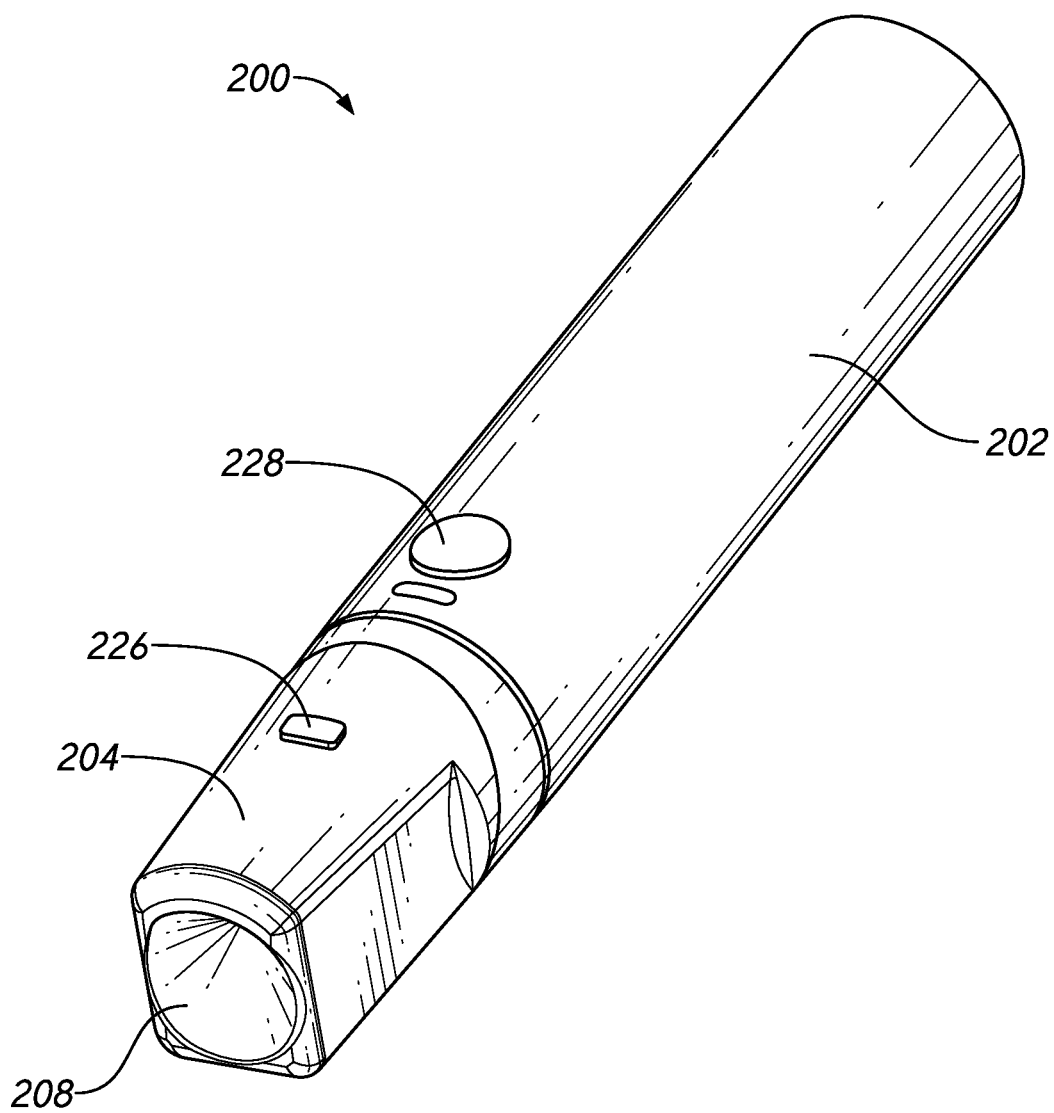
FIG. 4 shows an isometric view of a current generator, in accordance with one or more embodiments of the present technology.

FIGS. 4-10 illustrate several views of a current generator 200 according to one or more embodiments of the present technology. In operation, the current generator 200 is configured to slidably receive an end portion of an electrical cable (e.g., the core member 105 or other elongate conductor (s)) within the current generator 200. Once in position, the current generator 200 is electrically coupled to the cable (e.g., the first and/or second conductors 116, 118 of the core member 105) and can deliver electrical current thereto. As shown in FIG. 4, the current generator can include a body 202 and a cap 204. The cap 204 can be configured to couple to the body 202 at the distal end of the body 202. For example, the cap 204 can form a friction fit with the body 202 when the cap 204 slides over the distal end of the body 202 and interacts with an engagement portion 234 on the body 202. The body 202 can be configured to house the electronics of the current generator 200. For example, the body 202 can house a power source 240, a first electrical connector 222a, a second electrical connector 222b, a controller 242, and/or drive circuitry 248. As will be described in more detail below, in some embodiments, the body 202 can include a channel 206 on the distal end of the body 202. The channel 206 can provide an opening for a component, such as the core member, to be inserted within the current generator 200.

Figure 5:
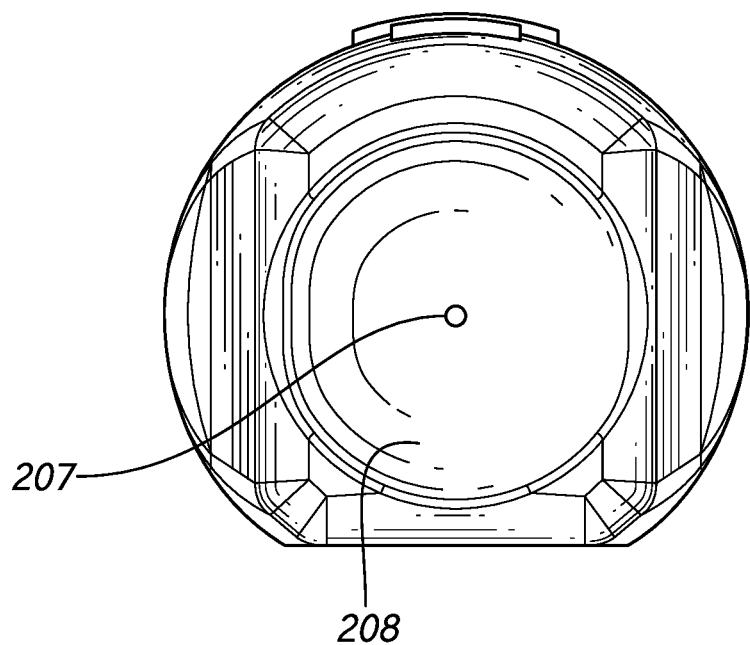
FIG. 5 shows a front view of a current generator, in accordance with one or more embodiments of the present technology.

As shown in FIGS. 4 and 5, the cap 204 can include an aperture 207 and a guide member or guide surface 208. The aperture 207 can be formed at or near the center of the guide surface 208. In some embodiments, the aperture 207 can be an opening that is coupled to and/or aligned with the channel 206 and provides access to the channel 206. The guide surface 208 can be formed on the distal end of the cap 204. In some embodiments, the guide surface 208 can be configured to guide a cable to the aperture 207. For example, the walls of the guide surface 208 can have a conical shape that leads to the aperture 207. The conical shape of the guide surface 208 directs any cable, or other object, that comes into contact with the guide surface 208 towards the aperture 207. In some embodiments, the guide surface 208 can be formed in another shape. For example, the guide surface 208 can have a hemispherical shape, a curved shape, and/or a sloped shape. In some embodiments, the guide surface 208 can have walls that taper towards the aperture 207 and/or towards the channel 206.

The current generator 200 can be configured to guide the core member 105 into the channel 206. For example, when a user attempts to insert the core member 105 into the current generator 200, the proximal end of the core member 105 can contact the guide surface 208, which can direct the proximal end of the core member 105 towards the aperture 207 due to the tapered shape of the guide surface 208. Once the core member 105 reaches the aperture 207, the core member 105 can be further inserted into the channel 206 through the aperture 207.

Figure 6:
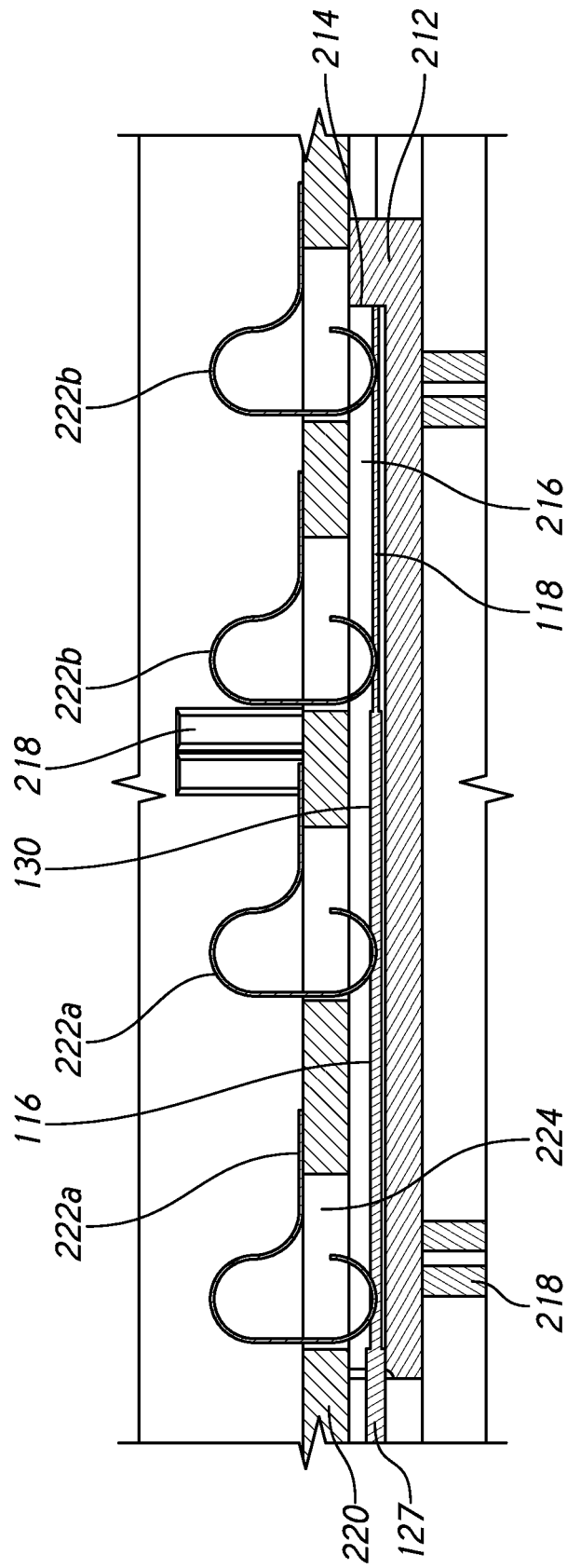
FIG. 6 shows a sectional view of a current generator, in accordance with one or more embodiments of the present technology.
Figure 7:
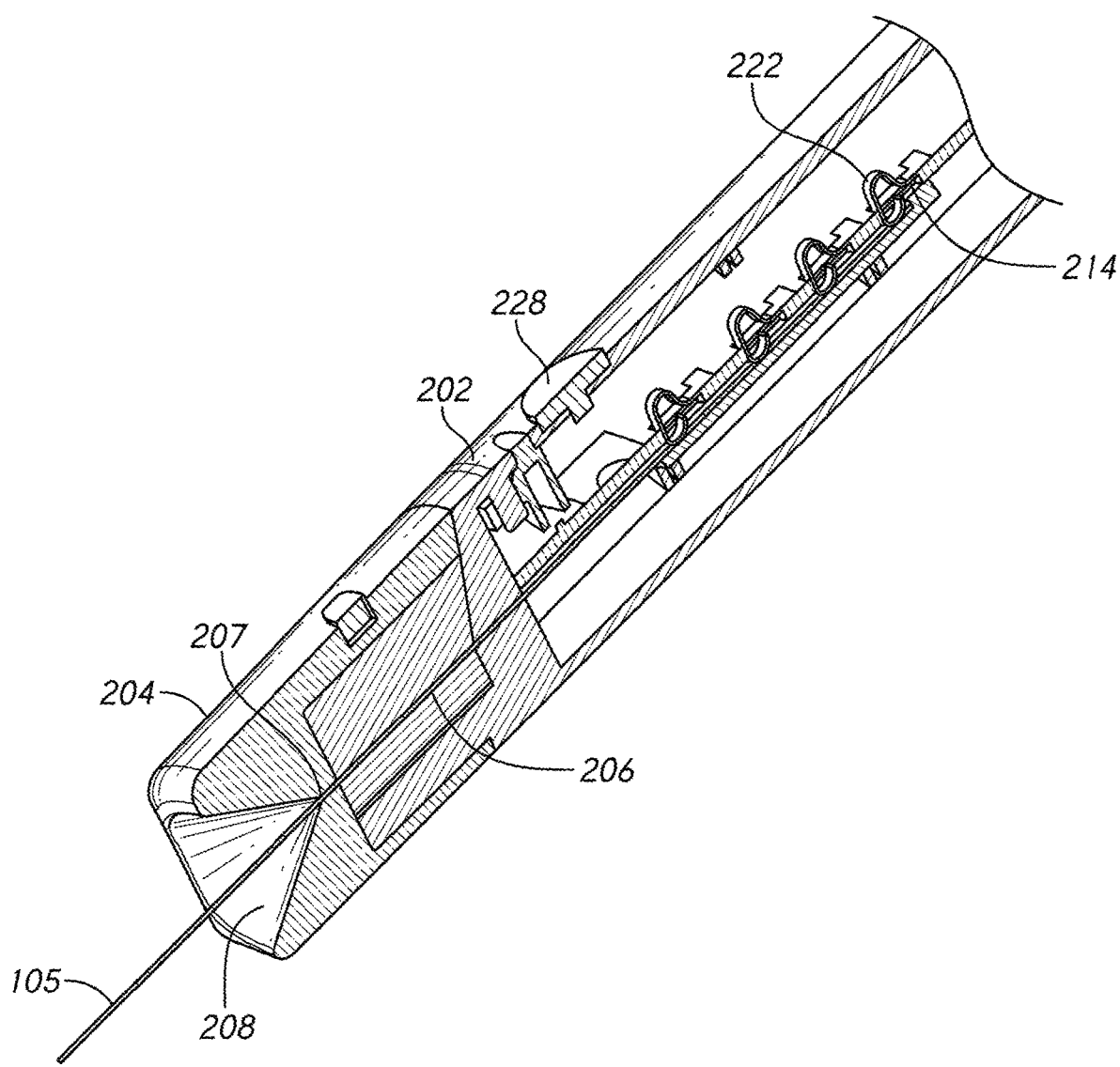
FIG. 7 shows a sectional view of a current generator, in accordance with one or more embodiments of the present technology.

FIGS. 6 and 7 illustrate several sectional views of the current generator 200 according to one or more embodiments of the present technology. As shown in FIGS. 6 and 7, in some embodiments, the current generator 200 can include a channel 206, a lower wall 212, a stop 214, an inner chamber 216, one or more spacers 218, an upper wall 220, and one or more electrical connectors 222. The channel 206 can be an opening that is formed on the distal end of the body 202 of the current generator 200. The opening of the channel 206 can extend through a portion of the body 202 and couple to the inner chamber 216 to provide access to the inner chamber 216. The inner chamber 216 can be defined by the space between the lower wall 212 and the upper wall 220. The lower wall 212 can have an end portion or stop 214. The stop 214 can mark the proximal end of the inner chamber 216. The upper wall 220 can be coupled to the lower wall 212. In some embodiments, the upper wall 220 can have one or more gaps 224 formed within the upper wall 220. In some embodiments, one or more electrical connectors 222 can extend through the one or more gaps 224 to be accessible within the inner chamber 216. In various embodiments, the electrical connectors 222 can be clips, wires, plugs, brushes, prongs, or other suitable connectors, or comprise electrically conductive surfaces, projections or members which are biased toward the channel 206. In some embodiments, one or more spacers 218 can be coupled to the lower wall 212 and upper wall 220.

The current generator 200 can be sized to hold at least a portion of the core member 105 within the current generator 200. For example, as shown in FIGS. 6 and 7, the proximal end of the core member 105 can be inserted into the current generator 200 through the aperture 207 so that a portion of the core member 105 is positioned within the channel 206 or both the channel 206 and inner chamber 216. In some embodiments, the inner chamber 216 is sized to hold the exposed contact regions of the core member 105 entirely within the inner chamber 216. For example, the length of the inner chamber 216 can equal or exceed the combined lengths of length 132, length 134, and length 136 as shown in FIG. 3. In some embodiments, the length of the inner chamber 216 can be greater than the combined lengths of length 132, length 134, and length 136. In some embodiments, the aperture 207 is sized to exclude components that are slightly larger (e.g. 10%, 5%, 1%, or less than 1% larger) than outer diameter of the core member 105. In some embodiments, the core member 105 has an outer diameter between the range of 0.01 inches to 0.03 inches. In various embodiments, the core member 105 has an outer diameter between the range of 0.014 to 0.027 inches. The current generator 200 can be configured to couple to the core member 105. For example, as shown in FIGS. 6 and 7, the core member 105 can be inserted within the inner chamber 216 of the current generator 200 through the aperture 207 and channel 206. In some embodiments, the current generator 200 can slide over a portion of the core member such that the core member 105 abuts the stop 214 of the lower wall 212.

In some embodiments, the current generator 200 can be configured to electrically couple to the core member 105. For example, as shown in FIGS. 6 and 7, when the core member 105 is inserted into the inner chamber 216, the exposed contact regions of the first conductor 116 and the second conductor 118 can come into contact with the electrical connectors 222, which establishes an electrical connection between the current generator 200 and the core member 105. As shown in FIG. 6, the first connectors 222*a* and second connectors 222*b* can come into contact with the exposed portions of the first conductor 116 and the second conductor 118 respectively when the core member 105 is inserted into the current generator 200. In some embodiments, the inner chamber 216 is sized and oriented relative to the connectors 222 so that exposed portions of the first conductor 116 and the second conductor 118 align and come into contact with the electrical connectors 222 when the proximal end of the core member 105 abuts the stop 214 of the lower wall 212. Because the exposed contact regions can align and come into contact with the electrical connectors 222 when the proximal end of the core member 105 abuts the stop 214, the current generator 200 can ensure a reliable electrical connection is formed between the current generator and core member 105. In some embodiments, the current generator 200 does not electrically couple to the core member 105 unless the proximal end of the core member 105 abuts the stop 214. For example, the channel 206, chamber 216 and/or connectors 222 can be configured such that the electrical connectors 222 contact an insulated portion of the core member 105 instead of the exposed contact regions when the proximal end of the core member 105 does not abut the stop 214.

In some embodiments, the electrical connectors 222 can be configured to couple to the exposed contact regions of the first conductor 116 and the second conductor 118. For example, as shown in FIG. 6, the first electrical connector 222*a* can contact the exposed portion of the first conductor 116 while the second electrical connector 222*b* can contact the exposed portion of the second conductor 118. In some embodiments, more than one electrical connector 222 can couple to the exposed portions of the first conductor 116 and second conductor 118. For example, as shown in FIG. 6, two first electrical connectors 222*a* can couple to the exposed portion of the first conductor 116 and two second electrical connectors 222*b* can couple to the exposed portion of the second conductor 118. In some embodiments, the electrical connectors 222 can have a curved engagement surface for engaging with the core member 105. When being inserted, the curved engagement surface can allow for the core member 105 to slide past the electrical connectors 222 without snagging or catching on a portion of the electrical connector 222. Additionally, the electrical connectors 222 can be resilient members that are biased downwardly such that they maintain physical contact with the core member 105 when it is positioned within the chamber 216. In some embodiments, as seen in FIG. 7, the electrical connectors 222 can have a width measured in a lateral direction orthogonal to longitudinal axis of the current generator 200 and/or the core member 105, and such width can be greater than (a) the width or diameter of the core member 105, and/or (b) the thickness of the material from which the connectors 222 are formed.

Figure 8:
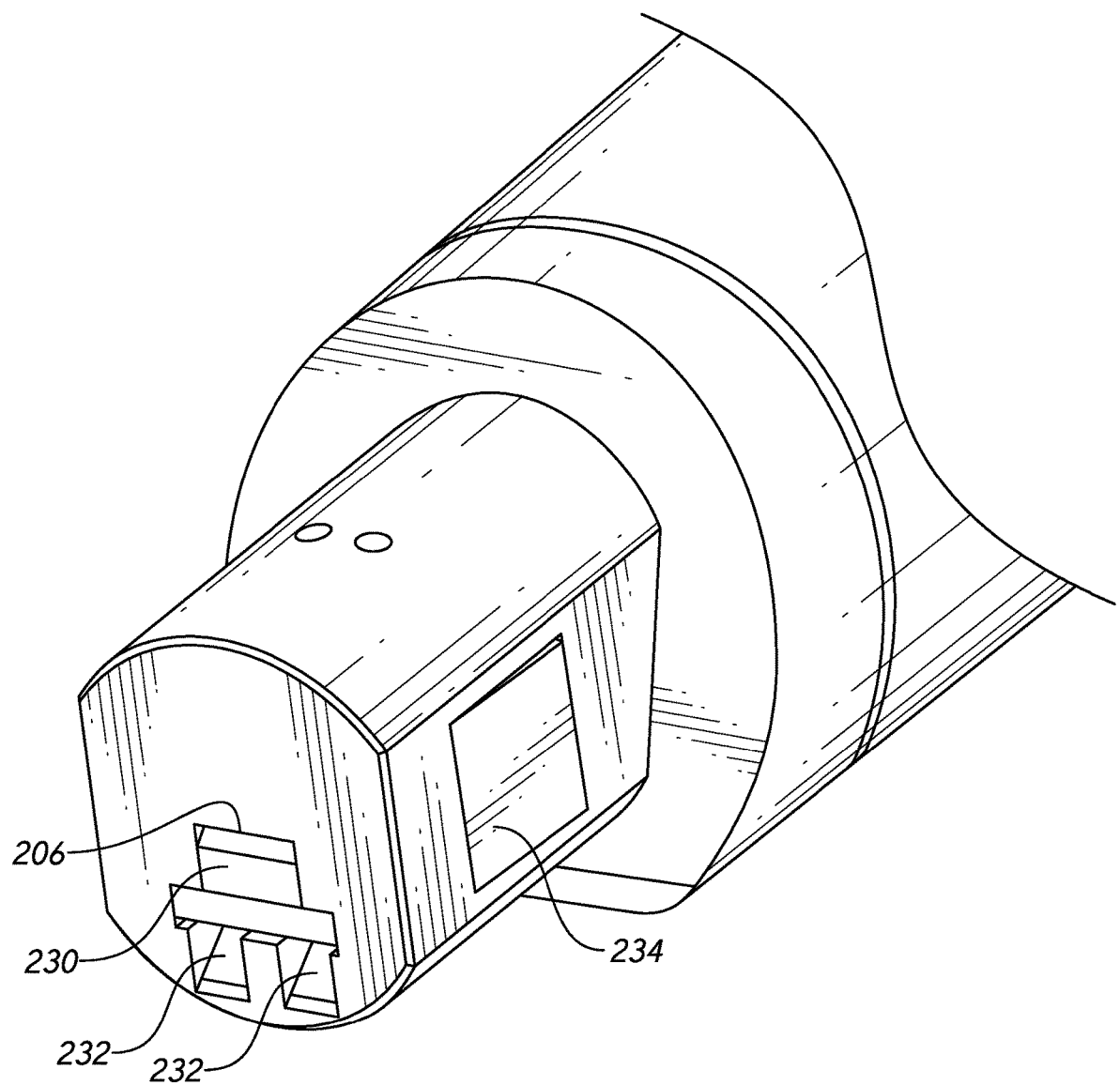
FIG. 8 shows an isometric view of a body of the current generator, in accordance with one or more embodiments of the present technology.
Figure 9:
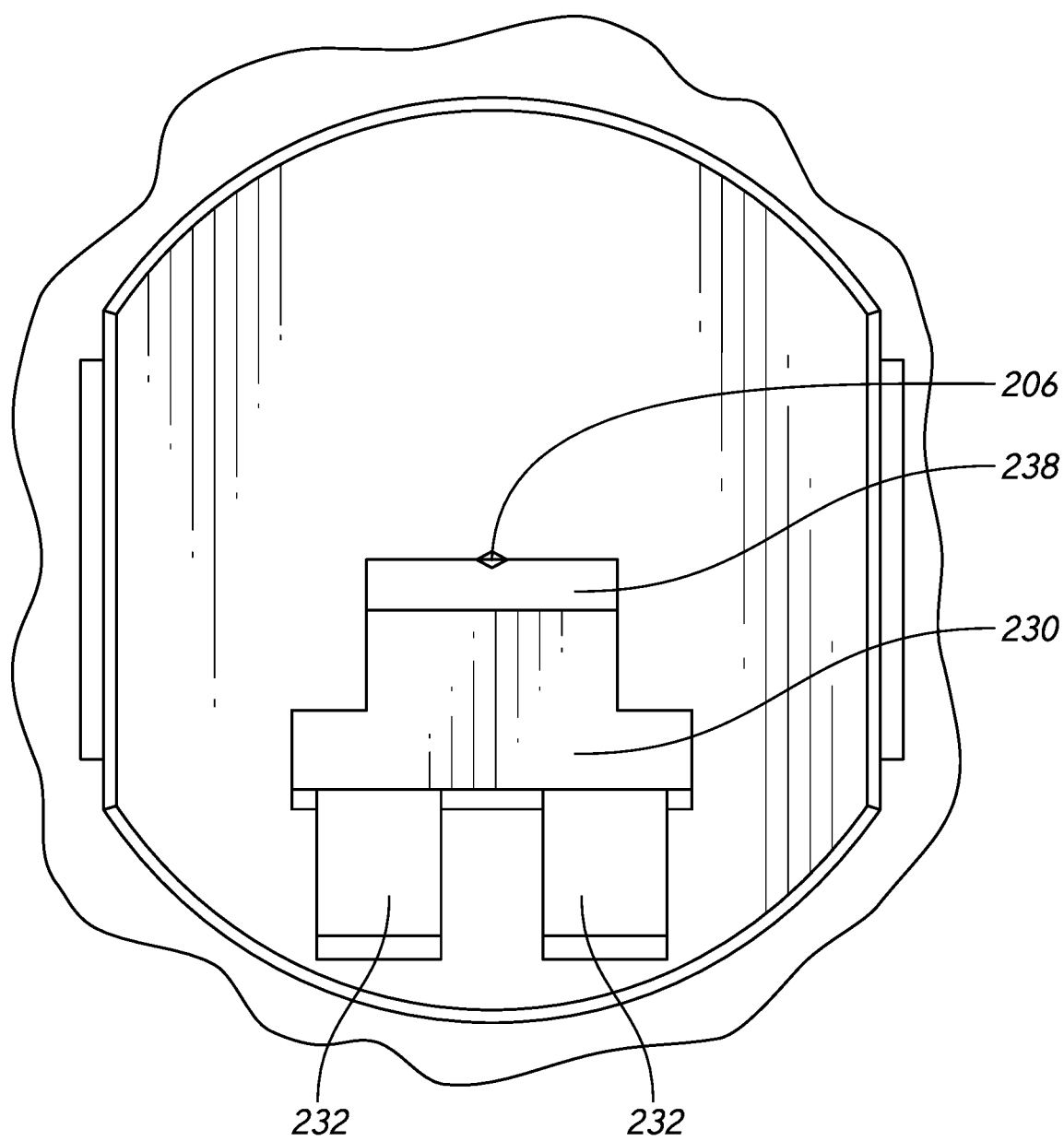
FIG. 9 shows a front view of the body of the current generator, in accordance with one or more embodiments of the present technology.
Figure 10:
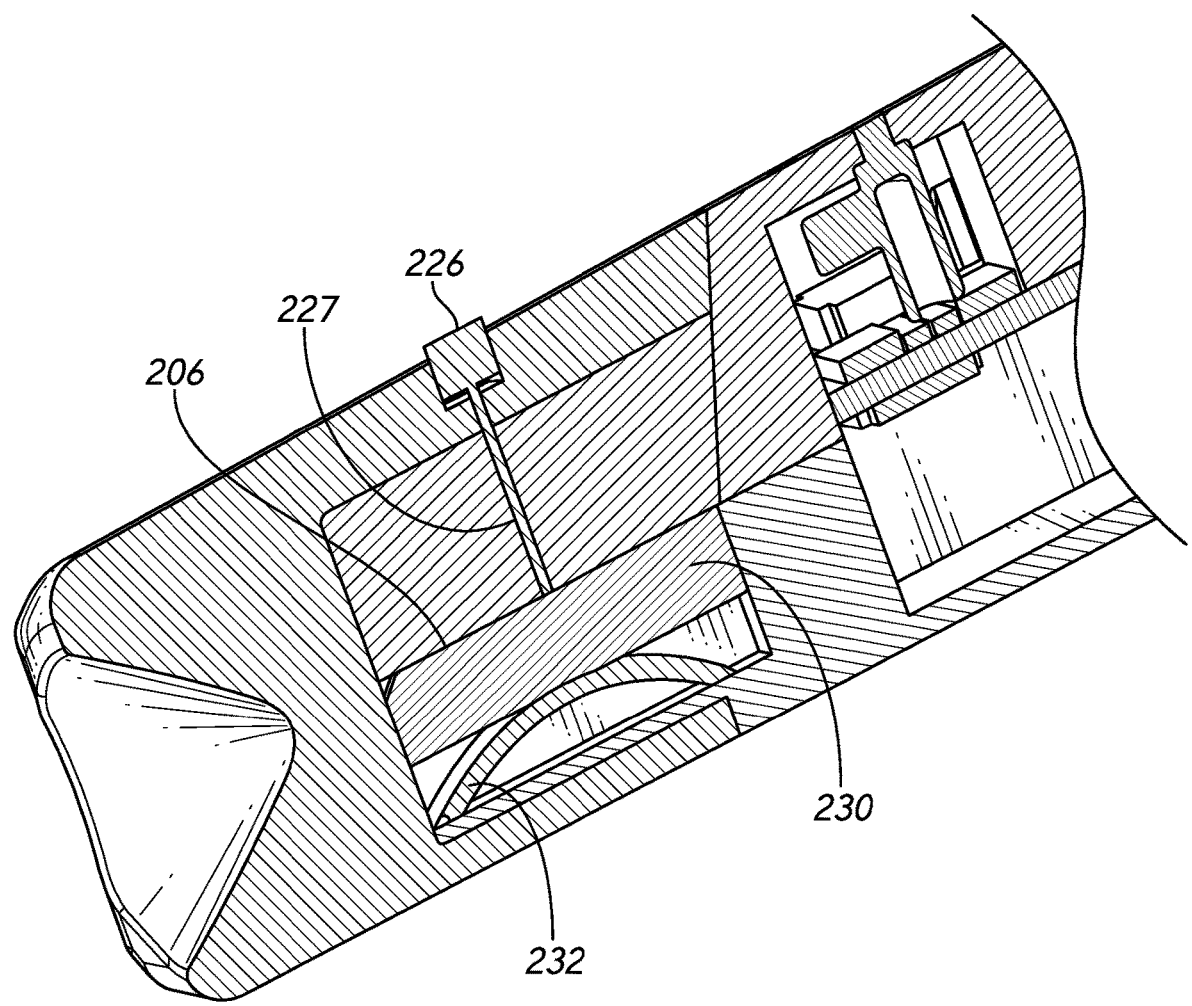
FIG. 10 shows a sectional view of a locking mechanism of a current generator, in accordance with one or more embodiments of the present technology.

As shown in FIGS. 8-10, the current generator 200 can include a locking member or cable lock. The locking member can include an insert 230, a biasing member 232, and a release mechanism 226. The insert 230 can be positioned at the distal end of the body 202. A top edge of the insert 230 can extend along all or a portion of the channel 206. In some embodiments, the insert 230 can include an angled edge or ramp 238 near or at the top of the insert 230, and/or at the proximal end of the insert 230. The angled edge or ramp can assist with directing the proximal end of the core member to the channel 206 during insertion of the core member. In some embodiments, the insert 230 can be moveable along an axis that intersects a longitudinal axis of the cable. For example, the insert 230 can be adjusted vertically so that the insert 230 intersects a longitudinal axis of the core member 105. The biasing member 232 can be coupled to, and/or bear against, the insert 230. The biasing member 232 is configured to bias the insert 230 towards the top wall of the channel 206. For example, as shown in FIG. 10, the biasing member 232 can be a spring that pushes the insert 230 towards the top wall of the channel 206. In some embodiments, the locking mechanism can include more than one biasing member 232. In various embodiments, the biasing member 232 is configured to bias the insert 230 away from the top wall of the channel 206. The release mechanism 226 can be a depressible button that is coupled to the insert 230 through one or more rods 227. The rods 227 can extend from the release mechanism 226 to couple with the insert 230. In some embodiments, the release mechanism 226 is integrally formed with the rods 227 and/or insert 230. The release mechanism 226 can be configured to adjust the insert 230 between a locked position and an unlocked position, where in the locked position the insert 230 is closer to top wall of the channel 206 when compared to the unlocked position. For example, when the release mechanism 226 is pressed in, the rods 227 can push downwards onto the insert 230, which can compress the biasing member 232 and results in the insert being in the unlocked position, as the insert is further away from the top wall of the channel 206. When the release mechanism 226 is released, the biasing member 232 can bias the insert 230 upwards, which results in the insert 230 being in the locked position as the insert 230 is closer to the top wall of the channel 206, and/or biased into that position by the biasing member 232. In some embodiments, the locking member can include an additional lock that holds the release mechanism 226 in its unlocked or locked position.

The current generator 200 can be configured to lock the core member 105 in place within the current generator 200 when the core member 105 is coupled to the current generator 200. For example, when the core member 105 is inserted into the current generator 200, the biasing member 232 can press the insert 230 against the portion of the core member 105 positioned within the channel 206 along the longitudinal axis of the core member 105. The insert 230 pressing against a portion of the core member 105 can create a friction fit with between the insert 230, the channel 206, and a portion of the core member 105. This friction fit can lock the core member 105 in position by preventing the core member 105 from moving, e.g., into or out of the channel 206 and/or current generator 200. In some embodiments, the friction fit is created when the release mechanism 226 is in its locked position. In some embodiments, the friction fit is released when the release mechanism 226 is in its unlocked state.

Figure 11:
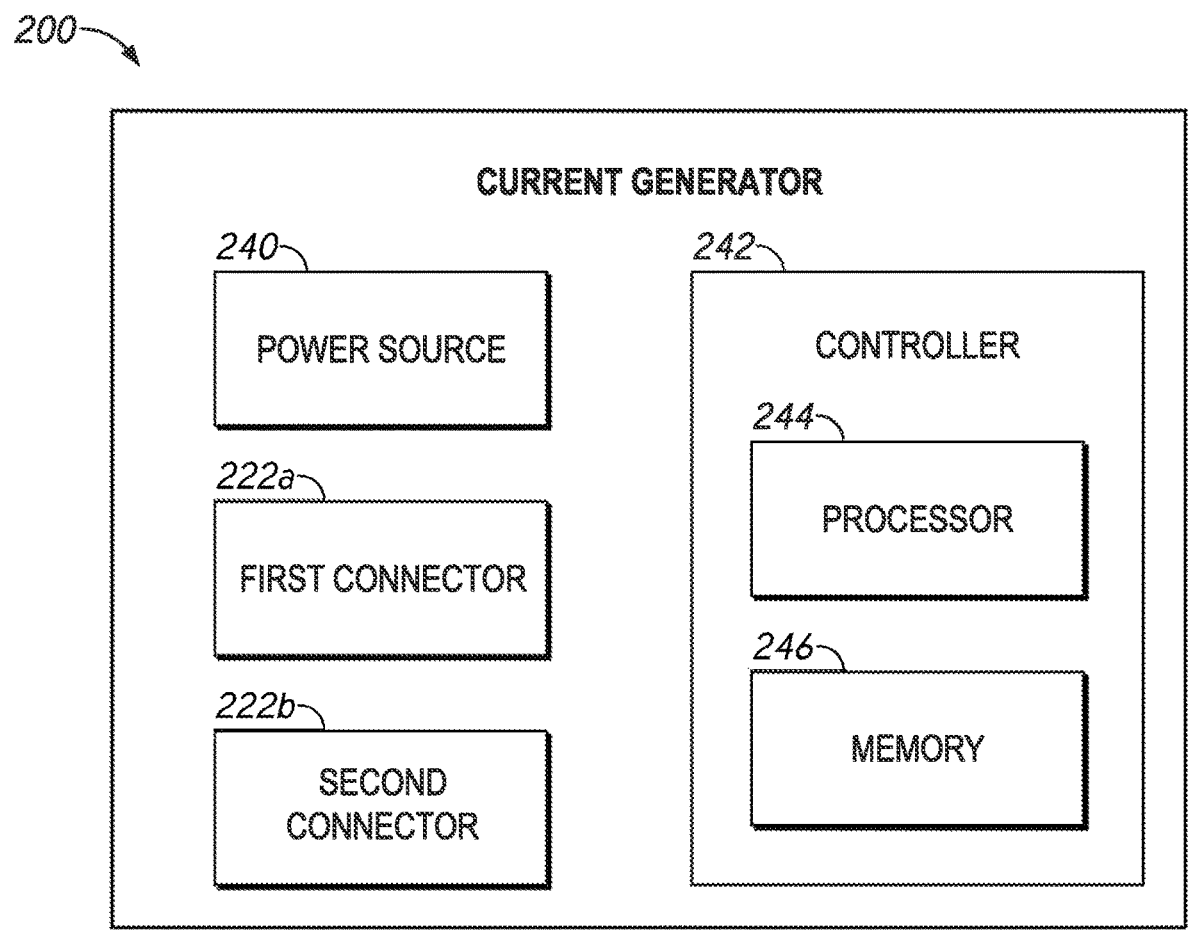
FIG. 11 shows a schematic view of the electronics of the current generator, in accordance with one or more embodiments of the present technology.
Figure 12:
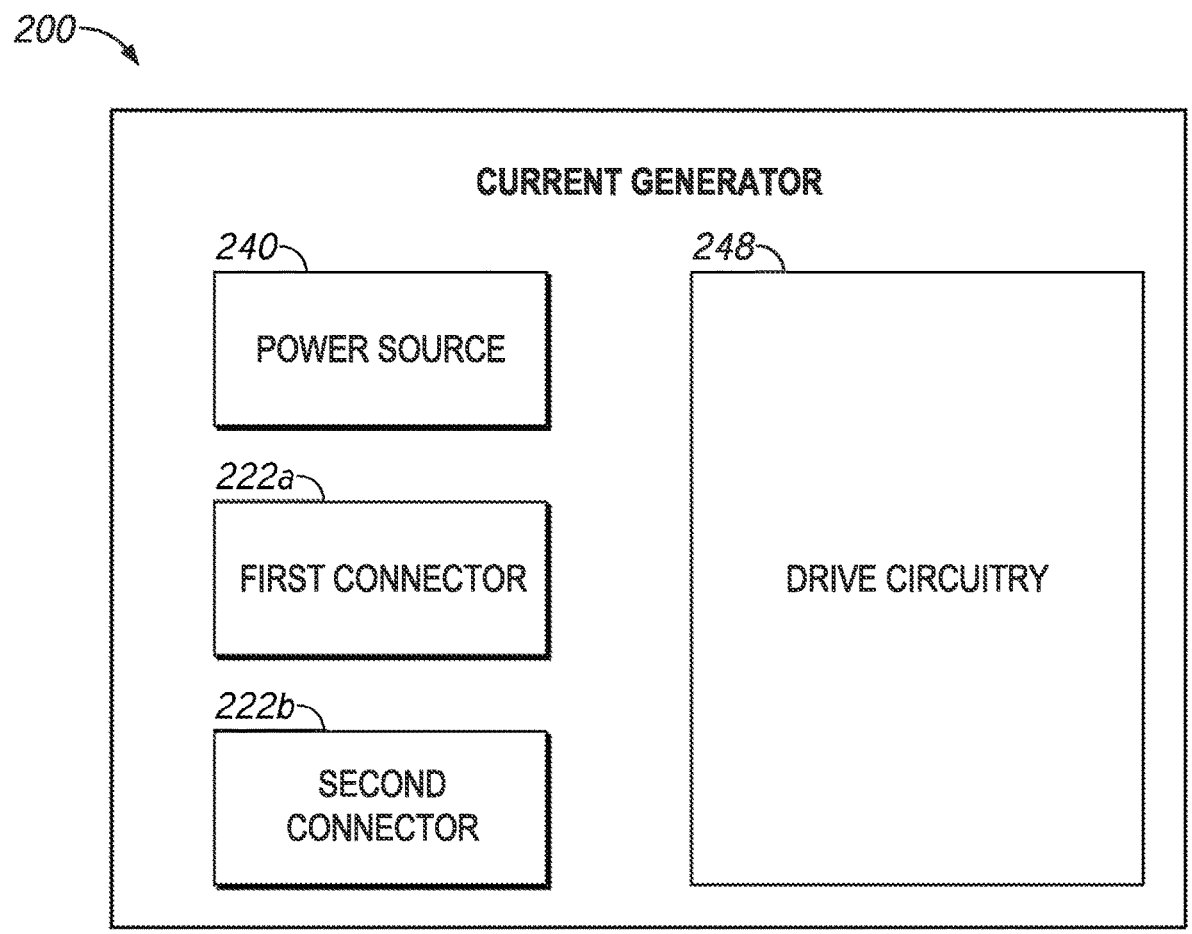
FIG. 12 shows a schematic view of the electronics of the current generator, in accordance with one or more embodiments of the present technology.

As shown in FIGS. 11 and 12, the current generator 200 can include a power source 240, a first electrical connector 222*a*, an (optional) second electrical connector 222*b*, a controller 242, and/or drive circuitry 248. The controller 242 can include a processor 244 coupled to memory 246 which stores instructions (e.g., in the form of software, code or program instructions executable by the processor or controller). In some embodiments, the processor 244 can execute instructions stored on the memory 246. For example, in some embodiments, the processor 244 can execute instructions stored on the memory 246 for causing the power source 240 to deliver electric current according to certain parameters provided by the software, code, etc. In some embodiments, the controller 242 can be used to control various parameters of the energy output by the power source 240 or generator, such as intensity, amplitude, duration, frequency, duty cycle, and polarity. For example, the controller 242 can adjust the current generator 200 to provide a voltage of about 2 volts to about 28 volts and a current of about 0.5 mA to about 20 mA. The power source 240 can be connected to the controller 242, the first electrical connector 222a, and the second electrical connector 222b. In some embodiments, the power source 240 may include a direct current power supply, an alternating current power supply, and/or a power supply switchable between a direct current and an alternating current. In some embodiments, the power source 240 can be a battery. In some embodiments, the power source 240 can deliver a current or other electrical signal to the first electrical connector 222a and the second electrical connector 222b. In some embodiments, instead of or in addition to a controller 242, the current generator 200 can include drive circuitry 248. In such embodiments, the current generator 200 can include hardwired circuit elements to provide the desired waveform delivery rather than a software-based generator. The drive circuitry 248 can include, for example, analog circuit elements (e.g., resistors, diodes, switches, etc.) that are configured to cause the power source 240 to deliver electric current via the first electrical connector 222a and the second electrical connector 222b according to the desired parameters. For example, the drive circuitry 248 can be configured to cause the power source 240 to deliver periodic waveforms via first electrical connector 222a and the second electrical connector 222b. In some embodiments, the current generator 200 can include one or more user interfaces. For example, as shown in FIG. 4, the body 202 can include a switch 228, which can be used to execute instructions stored in the memory 246 or turn the power on or off.

In some embodiments, the current generator 200 is configured to be a handheld device. For example, the current generator 200 can be sized so that the generator is capable of being held in the hand of a user. In some embodiments, the current generator 200 is not connected to an external power source, which can allow for the current generator to be utilized without connecting to an external power source.

The current generator 200 can be configured to output medically useful electric current to the treatment device 104. For example, when the current generator 200 is coupled to the core member 105, the switch 228 can be activated, which results in the power source 240 forming a circuit with the first electrical connector 222a, second electrical connector 222b, and the core member 105. With the circuit formed, the power source 240 can supply current to the treatment device 104 via the core member 105.

In various embodiments, the current generator 200 can include one or more safety systems that can prevent the current generator 200 from shorting or unintentionally shutting down. For example, the current generator 200 can run software that repeatedly checks the electrical path for current leakage or shortages. In some embodiments, the current generator 200 can include a feedback system that utilizes a user interface (e.g. sounds, lights, screen, etc.) to inform the user of any errors within the system. In various embodiments, the current generator 200 can be sealed to prevent moisture from entering into the current generator 200. For example, several components of the current generator 200 (e.g. the cap 204, release mechanism 226, and switch 228) can form a tight friction fit with the body 202 of the current generator 200, or can include a sealer (e.g. an O-ring) to prevent any unwanted moisture from entering into the conductive path. In some embodiments, the current generator 200 can include additional components to prevent an electrical signal from being unintentionally sent. For example, the current generator 200 can include a film that is placed over a terminal of a power source 140 to prevent the current generator 200 from operating until the film is removed.

An example method of using the current generator 200 to deliver an electrical signal to the treatment device 104 will now be described. First, the treatment device 104 is positioned within a patient at the treatment site or in a catheter, microcatheter, or in a sheath such as an introducer sheath (as can be used to package the treatment device 104) which may have a distal end configured for connection to a proximal end of a catheter hub. Once the treatment device 104 is properly positioned, the user can couple the core member 105 to the current generator. The core member 105 can be coupled to the current generator 200 by causing the current generator 200 to slide over the proximal end of the core member 105. The guide surface 208 can be used to guide the proximal end of the core member 105 to the aperture 207. Once the proximal end of the core member is at the aperture 207, the user can press the release mechanism 226 to place the insert 230 of the locking mechanism in the unlocked position. While in the unlocked position, the core member 105 can slide through the channel 206 and into the inner chamber 216. When the proximal end of the core member 105 abuts the stop 214, and/or aligns with the electrical connectors 222 of the current generator, the user can release the release mechanism 226 to place the insert 230 in the locked position, which locks the core member 105 in position. With the core member 105 in position, the user can interact with the switch 228. Interacting with the switch initiates the supply of an electrical signal through an electrical circuit from the power source 240, through the second electrical connector 222b, through the second conductor 118, to the treatment site, and returning from the treatment site, through the first conductor 116, through the first electrical connector 222a, and back to the power source 240. (When other forms or polarities of current are employed, the direction of travel may be in the opposite direction, or varied or alternating as appropriate.) In some embodiments, the electrical signal is an electrical current of between about 0-5 mA. In some embodiments, the electrical signal is supplied for a duration of time between about 30 seconds to about 10 minutes. After the electrical signal is delivered to the treatment device 104 for the proper duration, the user can interact with the switch 228 to deactivate the power source 240. Additionally, the user can press the release mechanism 226 to unlock the core member 105. With the core member 105 unlocked, the user can decouple the current generator 200 from the core member 105 by slidably removing the current generator 200 from the core member 105.

CONCLUSION

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

The invention claimed is:
1. A medical system comprising:
an elongate shaft comprising:
  a distal portion coupled to a medical device;
  a proximal portion;
  a first conductor including a first contact region at the proximal portion; and
  a second conductor having a second contact region at the proximal portion, the second contact region spaced apart from the first contact region; and
a current source configured to be releasably coupled to the elongate shaft and deliver an electrical signal to the first and second conductors, the current source comprising:
  an inner chamber configured to receive at least the proximal portion of the elongate shaft;
  a first electrical connector disposed within the inner chamber and configured to electrically connect with the first conductor via the first contact region;
  a second electrical connector disposed within the inner chamber and configured to electrically connect with the second conductor via the second contact region;
  a cable guide positioned at one end of the current source, the cable guide configured to guide the proximal portion of the elongate shaft to the inner chamber; and
  a cable lock configured to lock the proximal portion of the elongate shaft in position, wherein the cable lock comprises an insert, a biasing mechanism coupled to the insert, and a release mechanism, wherein the biasing mechanism is configured to press the insert against the proximal portion of the elongate shaft, and wherein the release mechanism comprises a rod configured to press downwardly on the insert to compress the biasing mechanism and temporarily move the insert away from the proximal portion of the elongate shaft.

2. The medical system of claim 1, wherein the elongate shaft is sized and configured to be advanced intravascularly to a treatment site.

3. The medical system of claim 1, wherein the first and second conductors are coaxial.

4. The medical system of claim 1, wherein the elongate shaft is a cable.

5. The medical system of claim 1, wherein the first conductor comprises a tubular member defining a lumen, and wherein the second conductor comprises an elongate member extending through the lumen.

6. The medical system of claim 1, further comprising an electrically insulative material disposed radially between the first conductor and the second conductor.

7. The medical system of claim 1, further comprising an electrically insulative material disposed axially between the first contact region and the second contact region.

8. The medical system of claim 1, wherein the first electrical connector comprises a clip configured to contact the first contact region when the proximal portion of the elongate shaft is received within the inner chamber, and wherein the second electrical connector comprises a second clip configured to contact the second region when the proximal portion of the elongate shaft is received within the inner chamber.

9. The medical system of claim 1, wherein the current source is a current generator.

10. The medical system of claim 1, wherein the inner chamber comprises a proximal stop configured such that when the proximal portion of the elongate shaft is slidably disposed within the inner chamber such that a proximal end of the elongate shaft abuts the proximal stop, the first and second contact regions are in contact with the first and second connectors, respectively.

11. The medical system of claim 1, wherein the cable guide comprises a guide surface adjacent an aperture, the guide surface configured to urge a proximal end of the elongate shaft through the aperture.

12. The medical system of claim 11, wherein the guide surface is at least one of: tapered, curved, sloped, or conical.

13. The medical system of claim 1, wherein the biasing mechanism comprises a spring.

14. The medical system of claim 1, wherein the release mechanism comprises a depressible button.

15. The medical system of claim 14, wherein the depressible button is integrally formed with the insert.

16. A current generator for a medical device including a core member, the current generator comprising:
  a body having a first end, a second end opposite the first end, and an inner chamber extending from the first end towards the second end, the inner chamber being configured to slidably connect to the core member and being configured to hold at least a part of the core member therein;
  an electrical connector disposed at least partially within the inner chamber, the electrical connector configured to electrically connect with the core member;
  a guide member positioned at the first end, the guide member configured to guide the at least a part of the core member to the inner chamber; and
  a locking member configured to releasably retain the at least a part of the core member in position, wherein the locking member comprises an insert, a biasing mechanism coupled to the insert, and a release mechanism, wherein the biasing mechanism is configured to press the insert against the at least a part of the core member, and wherein the release mechanism comprises a rod configured to press downwardly on the insert to compress the biasing mechanism and temporarily move the insert away from the at least a part of the core member.

17. The current generator for a medical device of claim 16, wherein the electrical connector comprises a clip configured to contact the core member.

18. The current generator for a medical device of claim 16, further comprising a second electrical connector disposed at least partially within the inner chamber.

19. The current generator for a medical device of claim 16, wherein the inner chamber comprises a proximal stop configured to abut a proximal end of the core member such that when the core member abuts the proximal stop, the electrical connector electrically connects with the core member.

* * * * *